US008728438B2

(12) United States Patent
Pieters et al.

(10) Patent No.: US 8,728,438 B2
(45) Date of Patent: May 20, 2014

(54) CORONIN 1 MODULATORS FOR THE TREATMENT OF AUTOIMMUNE AND LYMPHOPROLIFERATIVE DISORDERS AND MYCOBACTERIAL INFECTIONS

(71) Applicant: University of Basel, Basel (CH)

(72) Inventors: Jean Pieters, Riehen (CH); Rajesh Jayachandran, Basel (CH)

(73) Assignee: University of Basel, Basel (CH)

( * ) Notice: Subject to any disclaimer, the term of this patent is extended or adjusted under 35 U.S.C. 154(b) by 0 days.

(21) Appl. No.: 13/953,134

(22) Filed: Jul. 29, 2013

(65) Prior Publication Data

US 2013/0336966 A1 Dec. 19, 2013

Related U.S. Application Data

(63) Continuation of application No. 12/225,538, filed as application No. PCT/EP2007/052793 on Mar. 23, 2007, now Pat. No. 8,518,372.

(30) Foreign Application Priority Data

Mar. 24, 2006 (EP) .................................... 06111702
Oct. 3, 2006 (EP) .................................... 06121685

(51) Int. Cl.
*A61K 49/00* (2006.01)
*A61K 39/00* (2006.01)
*A61K 39/395* (2006.01)

(52) U.S. Cl.
USPC ....... 424/9.1; 424/9.2; 424/130.1; 424/139.1; 424/185.1; 424/234.1

(58) Field of Classification Search
USPC ........ 424/9.1, 9.2, 130.1, 139.1, 185.1, 234.1
See application file for complete search history.

(56) References Cited

FOREIGN PATENT DOCUMENTS

WO 03/040296 5/2003

OTHER PUBLICATIONS

John Gatfield et al., "Association of the Leukocyte Plasma Membrane with the Actin Cytoskeleton through Coiled Coil-mediated Trimeric Coronin 1 Molecules", Molecular Biology of the Cell, vol. 16, pp. 2786-2798 (2005).
Béatrice Nal et al., "Coronin-1 expression in T lymphocytes: insights into protein function during T cell development and activation", International Immunology, vol. 16, No. 2, pp. 231-240 (2003).
Database WPI week 200446, Derwent Publications Ltd., London, GB; AN 1996-283507—Abstract of JP 03-542181 B2 (2004).
Vincent Das et al., "Membrane-cytoskeleton interactions during the formation of the immunological synapse and subsequent T-cell activation", Immunological Reviews, vol. 189, pp. 123-135 (2002).
H.F. Geerdes-Fenge et al., "Effects of IL-10, prednisolone, and cyclosporin A on the resistance of C57BL/6 mice to Mycobacterium avium infection", Abstr. Intersci. Conf. Antimicrob Agents Chemother Intersci Conf Antimicrob. Agents Chemother, Sep. 15-18; 145 (Abstract No. G14)(1996).
Miyoko Tanaka et al., "Effects of Cyclosporin A on Bacterial Growth and Immunological Responsiveness in BALB/c Mice Infected with Mycobacterium Leprae", International Journal of Leprosy, vol. 59, No. 4, pp. 598-604 (1991).
Gutierrez, Maximiliano G., et al., "Autophagy is a Defense Mechanism Inhibiting BCG and Mycobacterium tuberculosis Survival in Infected Macrophages", Cell, vol. 119, 2004, pp. 753-766.
Haraldsson, M. Katarina, et al., "The Lupus-Related Lmb3 Locus Contains a Disease-Suppressing Coronin-1A Gene Mutation", Immunity, vol. 28, 2008, pp. 40-51.
Siegmund, Kerstin, et al., "Coronin 1-Mediated Naive T Cell Survival is Essential for the Development of Autoimmune Encephalomyelitis", The Journal of Immunology, 2011, pp. 1-10.
Greenspan et al. (Nature Biotechnology 7: 936-937, 1999).
Bowie et al.; (Science, 1990, 257:1306-1310).
Takashima et al (Infection and Immunity, Jul. 1987, vol. 55, No. 7, p. 1701-1706).
Nal et al (International Immunology, 2003, vol. 16, No. 2, p. 231-240).
Tanaka et al (International Journal of Leprosy, 1991, vol. 59, No. 4, p. 598-604 ).
Pozzilli et al (Diabetes Care 24, pp. 1460-1467, 2001).
Ferrari, G., et al. Cell, vol. 97, pp. 435-447, 1999.
Vyse, T.J. Immunity, vol. 28, No. 1, pp. 8-10, 2008.

*Primary Examiner* — Rod P Swartz
(74) *Attorney, Agent, or Firm* — Wenderoth, Lind & Ponack, L.L.P.

(57) ABSTRACT

The invention relates to the treatment of mycobacterial infections, autoimmune disorders, lymphoproliferative disorders and induction of immunosuppression following transplantation using coronin 1 and modulators of coronin 1. Particular modulators of coronin 1 are compounds which inhibit the production of coronin 1 or the formation of active coronin 1 from a coronin 1 precursor, partly or entirely inactivate coronin 1, inhibit concentration of coronin 1 at the site of T cell activation, or inhibit the coronin 1 mediated signaling pathway downstream of the T cell receptor. Examples of such modulators are antibody or antibody fragments, coronin 1 peptide fragments or corresponding phosphopeptides, or anti-sense oligonucleotides, e.g. siRNA or shRNA. The invention further relates to a method of screening for a compound effective in the treatment of mycobacterial infections, autoimmune disorders, lymphoproliferative disorders and induction of immunosuppression following transplantation comprising contacting a candidate compound with coronin 1 or coronin 1 expressing cells, and selecting appropriate compounds.

6 Claims, 19 Drawing Sheets e f g h

CORONIN 1 MODULATORS FOR THE TREATMENT OF AUTOIMMUNE AND LYMPHOPROLIFERATIVE DISORDERS AND MYCOBACTERIAL INFECTIONS

This application is a continuation of U.S. Ser. No. 12/225,538, filed Sep. 24, 2008, now U.S. Pat. No. 8,518,372, which is a national stage application of PCT/EP2007/052793, filed Mar. 23, 2007, the entireties of which are incorporated by reference.

FIELD OF THE INVENTION

This invention relates to the treatment of mycobacterial infections, autoimmune disorders, lymphoproliferative disorders and induction of immunosuppression following transplantation using modulators of coronin 1.

BACKGROUND OF THE INVENTION

T cell homeostasis is central to the ability of vertebrate organisms to mount an effective immune response. Lymphocyte precursors, originating from the bone marrow, home to the thymus, where negative and positive selection results in the production of CD4 or CD8 single positive T lymphocytes. From the thymus, single positive T lymphocytes seed the peripheral organs, where they cycle for prolonged times between the secondary lymphoid organs and the blood in a naïve state. Following infection, T cells become activated by dendritic cells within peripheral lymph nodes, which induces massive proliferation of so-called effector T cells. After the infection has been cleared, effector cells have to be eliminated in order to maintain peripheral T cell homeostasis.

The signals that are responsible for the selection, proliferation and survival of T cells rely on stimulation of the T cell receptor by major histocompatibility complex (MHC) molecules that are present on antigen presenting molecules. While in the thymus, positive selection selects those thymocytes recognizing self-MHC molecules, negative selection ensures the elimination of those T cells that strongly recognize self-peptides in the context of self-MHC. Together, these selection processes within the thymus ensure the generation of naïve, non-autoreactive T cells for population of peripheral organs.

Once in the periphery, however, T cells need to be maintained in a naïve state while retaining the capacity to rapidly respond to an infection. Also these processes are regulated through activation of T cell receptors, both for the induction of T cell proliferation following an infection as well as for maintaining the naïve T cell population. While the distinction between life and death of a T cell appears to be controlled by the type of interaction with MHC molecules (A. Singer, Curr Opin Immunol 2002, 14, 207-215, A. Lanzavecchia and F. Sallusto, Curr Opin Immunol 2002, 12, 92-98), the molecular components involved in this decision are largely unknown.

Coronin 1 is also termed P57 or TACO (for tryptophan aspartate containing coat protein (G. Ferrari et al., Cell 1999, 97, 435-447). Coronin 1 is an F-actin interacting protein that is transcribed in all cells of the haematopoeitic lineage. Coronin 1 is a member of the WD repeat family of coronin proteins that are widely expressed in the eukaryotic kingdom (E. L. de Hostos, Trends Cell Biol 1999, 9, 345-350; J. Gatfield et al., Mol Biol Cell 2005, 16, 2786-2798). Whereas in *Dictyostelium*, which contains a single coronin gene, coronin is involved in actin-dependent processes such as phagocytosis, cell migration and cytokinesis (E. L. de Hostos et al., EMBO J 1991, 10, 4097-4104; M. Maniak et al., Cell 1995, 83, 915-924), in mammalian cells no biological activity has been assigned to any of the coronin homologues.

*Mycobacterium* spp. are highly successful pathogens that evade innate immunity by manipulating the host to ensure long term survival. A role of TACO (Coronin 1) was suggested for mycobacteria survival within macrophage phagosomes (G. Ferrari et al., loc. cit.).

SUMMARY OF THE INVENTION

The present invention relates to a method of treating mycobacterial infections, autoimmune disorders, lymphoproliferative disorders and induction of immunosuppression following transplantation comprising administering coronin 1 or a modulator of coronin 1, and the use of coronin 1 and coronin 1 modulators in said treatment and in the manufacture of medicaments for treating mycobacterial infections, autoimmune disorders, lymphoproliferative disorders and induction of immunosuppression following transplantation. Furthermore the invention relates to a method of treating mycobacterial infections with calcineurin modulators such as cyclosporin A and tacrolimus (FK506).

The invention further relates to a method of screening for a compound effective in the treatment of mycobacterial infections, autoimmune and lymphoproliferative disorders comprising contacting a candidate compound with coronin 1 or a coronin 1 expressing cell, and choosing candidate compounds which selectively modulate activity of coronin 1 or lead to reduced or enhanced expression of coronin 1. The invention further relates to compounds selected by these methods of screening.

Coronin 1 is essential for survival of naive T cells in the periphery. In the absence of coronin 1, T cells are largely depleted from the periphery as they undergo apoptosis in the secondary lymphoid organs. Coronin 1 is therefore a specific survival factor for peripheral T cells. Furthermore, coronin 1 is implicated in the survival of mycobacteria in macrophages. Modulators of coronin 1 are compounds useful to treat mycobacterial infections, autoimmune as well as lymphoproliferative disorders. Coronin 1 modulators influence the calcineurin pathway. Other calcineurin modulators such as cyclosporin A and FK506 are likewise useful compounds to treat mycobacterial infections.

Coronin 1 expression in cells of the haematopoietic lineage. Single cell suspension prepared from the different organs (BM: Bone Marrow; Th: Thymus; Sp: Spleen; LN: Lymph Nodes) indicated and stained for the lymphocyte markers indicated followed by FACScan analysis.

Figure 2:
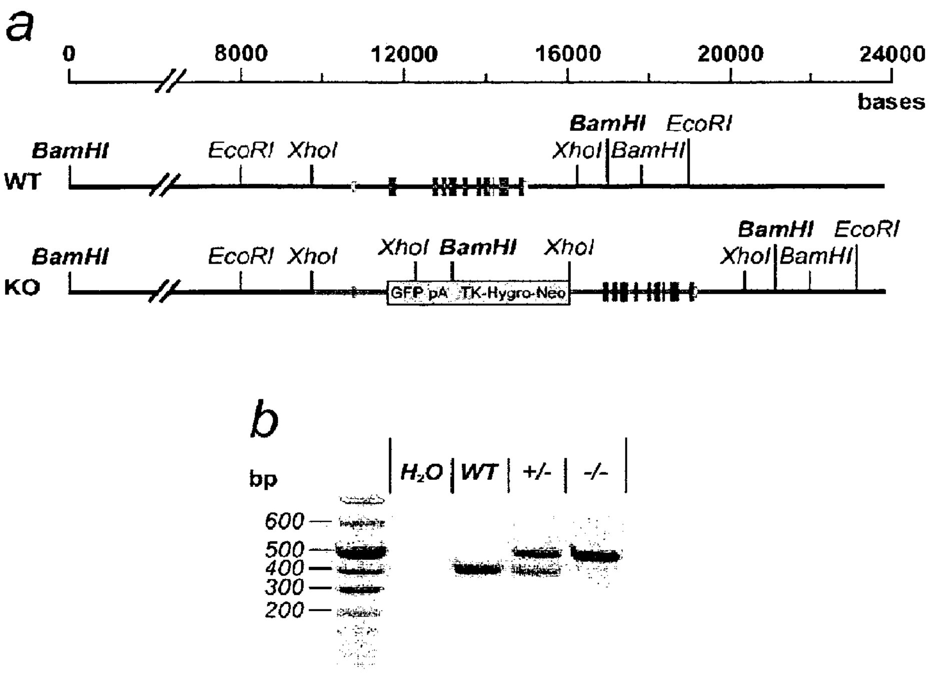
Figure 2:
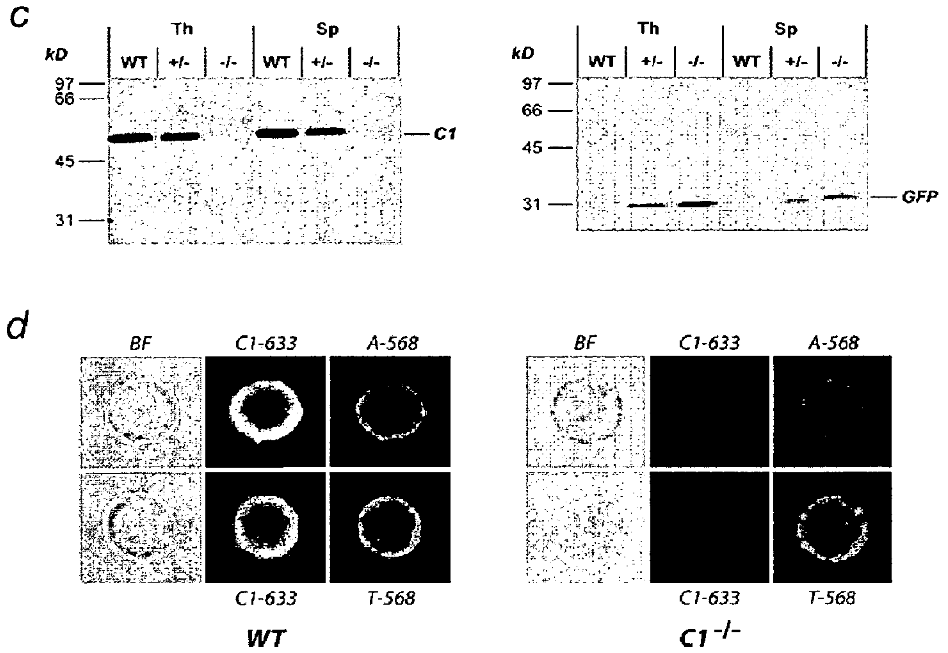

FIG. 2: Generation of coronin 1 deficient mice (a) Schematic representation of the genomic organization of the coronin 1 wild type (WT) and knock-out (KO) locus. The coronin 1 wild type (WT) locus consists of 11 exons of which exon 1 and 11 encode the 5'- and 3'-untranslated regions (UTR), respectively. Exon 2 contains the start codon. The coronin 1 knock-out (KO) locus was generated by specifically targeting exon 2 of the coronin 1 gene in mouse embryonic stem (ES) cells. The construct employed comprised of flanking homology regions to allow homologous recombination. After successful integration, exon 2 of coronin 1 is replaced by the open reading frame for EGFP which will result in expression of EGFP as a reporter under the control of coronin 1 regulatory elements. The sequence encoding EGFP is followed by a neomycin resistance marker (TK-Hygro-Neo) to allow the selection of positive ES cell clones for subsequent blastocyst injection.

(b) Analysis of mice by PCR.

(c) Cell lysates were prepared from the Thymus (Th) and spleen (Sp), and equal protein amounts separated by SDS-PAGE and immunoblotted for the detection of coronin 1 (left panel) and GFP (right panel).

(d) Wild type (WT, left panels) or coronin $1^{-/-}$ deficient (right panels) thymocytes were allowed to adhere to polylysine coated slides, fixed with paraformaldehyde and permeabilized prior to staining using phalloidin-568, as well as antibodies against tubulin and coronin 1 followed by Alexa-Fluor 568 and -633 labeled secondary antibodies, respectively. BF: Bright Field; A: actin; C1: Coronin 1.

Figure 3:
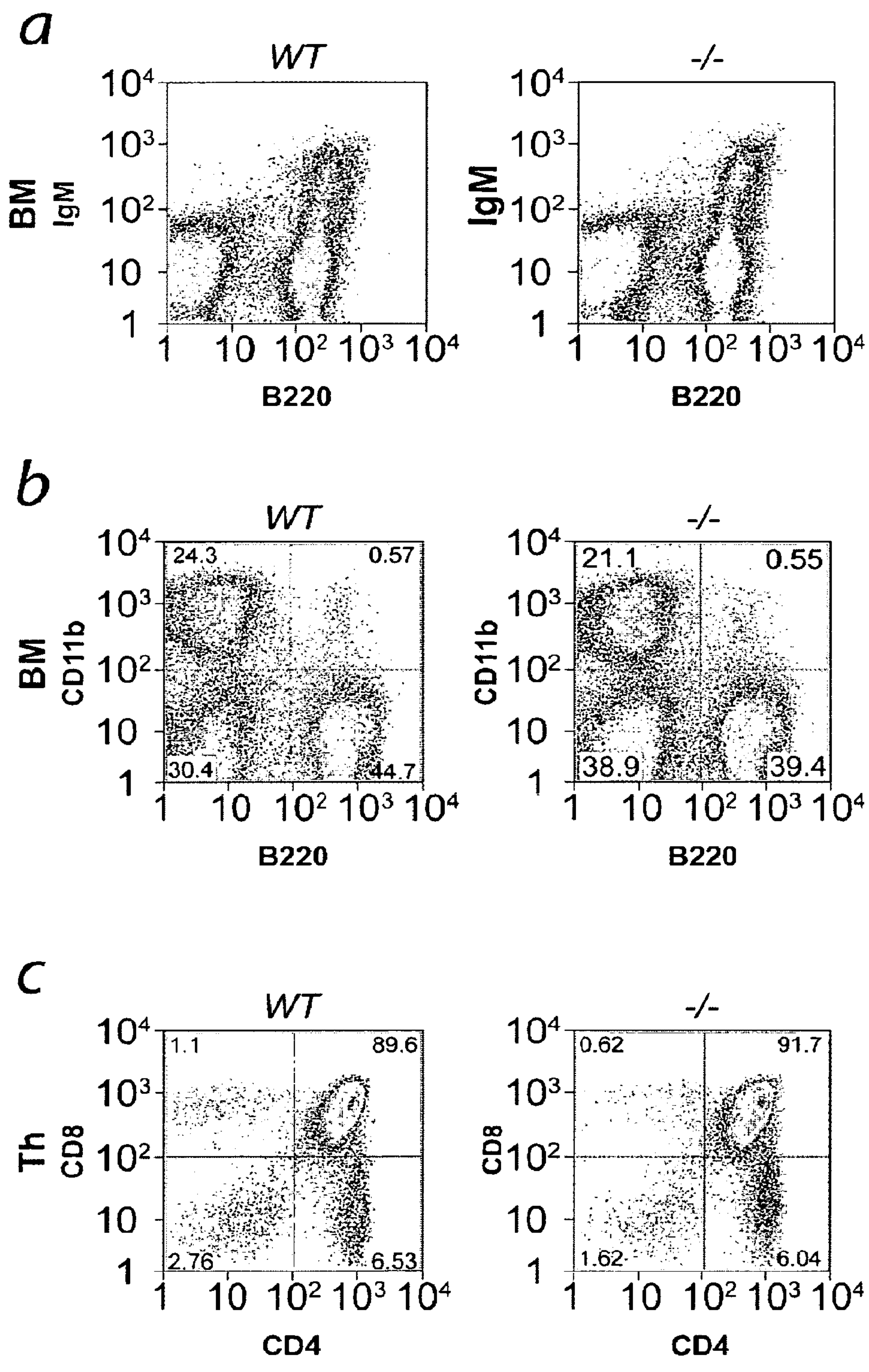
Figure 3:
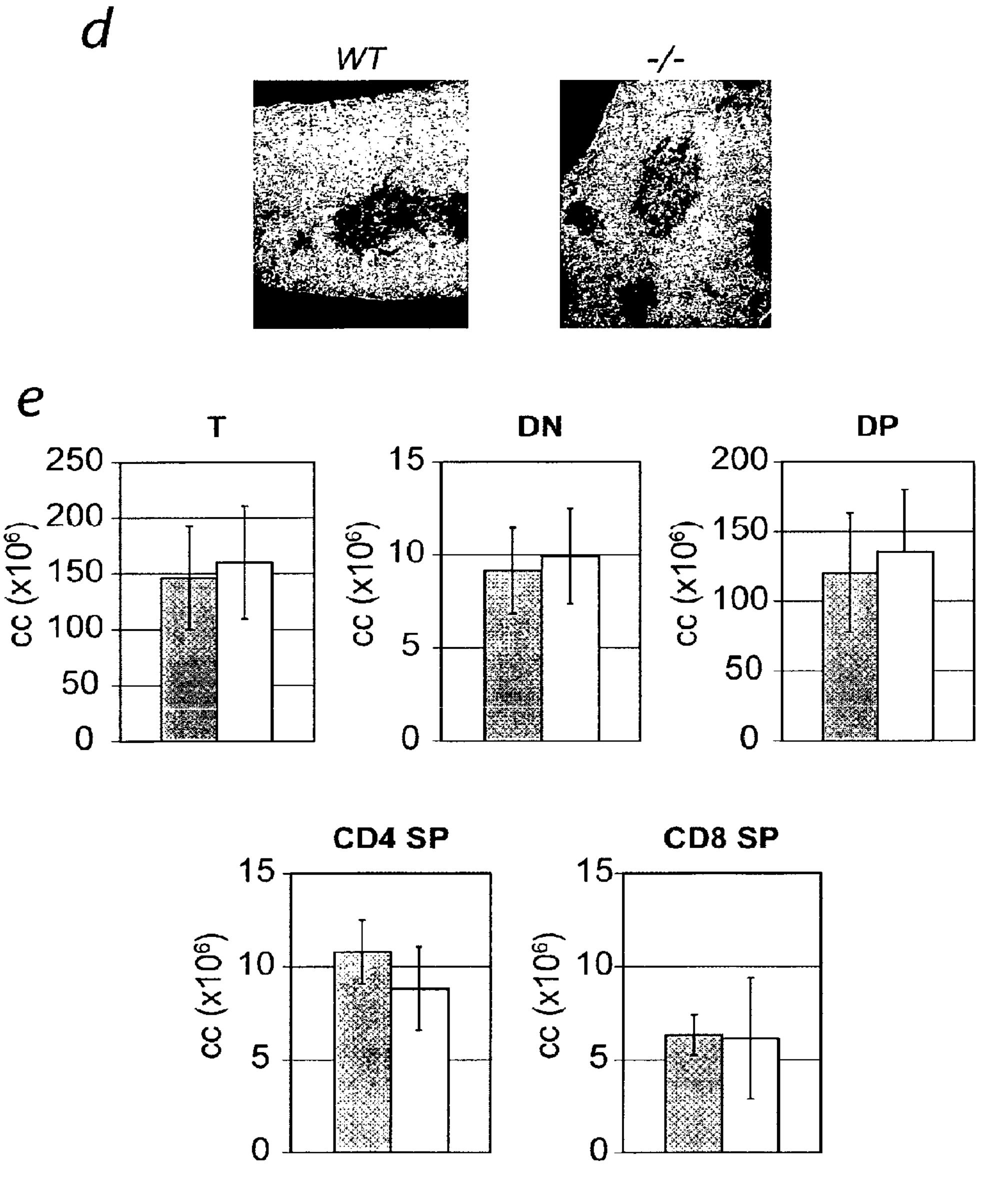

FIG. 3: Analysis of the development of the immune system in wild type (WT) and homozygous (−/−) coronin 1 knock-out mice.

Single cell suspensions of the indicated organs (BM: Bone Marrow; Th: Thymus) were prepared and stained with antibodies directed against antigens being specifically expressed at the various developmental stages of the lymphoid and myeloid lineage.

(a) Bone marrow cells were stained for the B-cell lineage marker B220 and IgM.

(b) Cells of the myeloid lineage were characterized by expression of CD11 b and B220.

(c) T-lymphocyte populations were analyzed by CD4 and CD8 staining.

(d) Thymi from WT (+/+) or coronin 1 deficient (−/−) mice were prepared for histology and stained for CD4 as well as CD8 cells using antibodies coupled to APC (CD4) or FITC (CD8). Magnification: 10×.

(e) Cell suspensions of the thymus of 6 weeks old homozygous (−/−) or wild type (WT) coronin 1 knock-out mice were analyzed by flow cytometry using antibodies directed against the indicated thymocyte subsets (CD4/CD8 double-negative (DN), double-positive (DP) and single-positive (SP) thymocytes). Cells were counted using a Neubauer chamber. Subset specific cell numbers were calculated by referring the percentage of a certain cell type (determined by flow cytometry) to the total cell counts. Total (T) and subset specific thymocyte cell counts. Filled bars: wild type, open bars: knock-out. Cc: cell counts. Data are means+/−SD of 5 animals (n=5).

Figure 4:
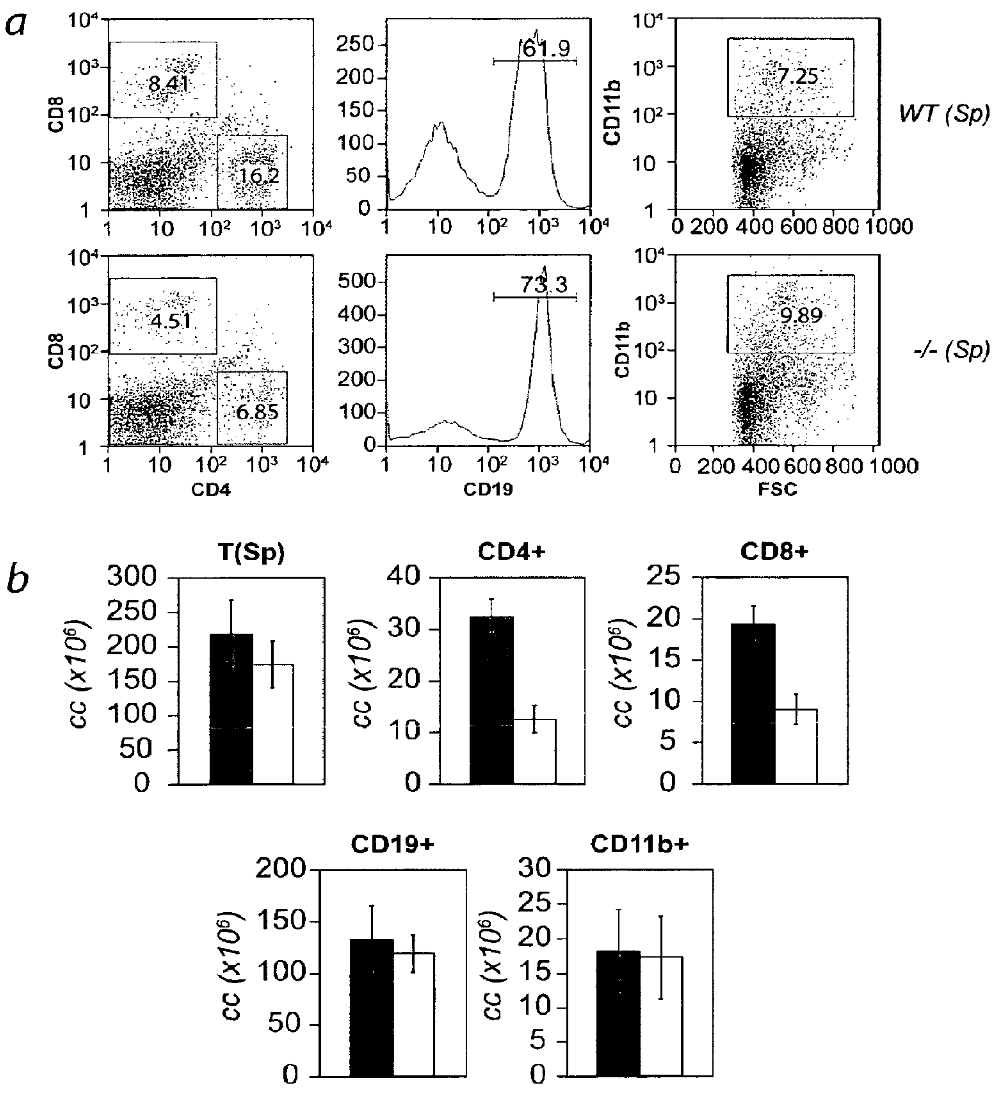
Figure 4:
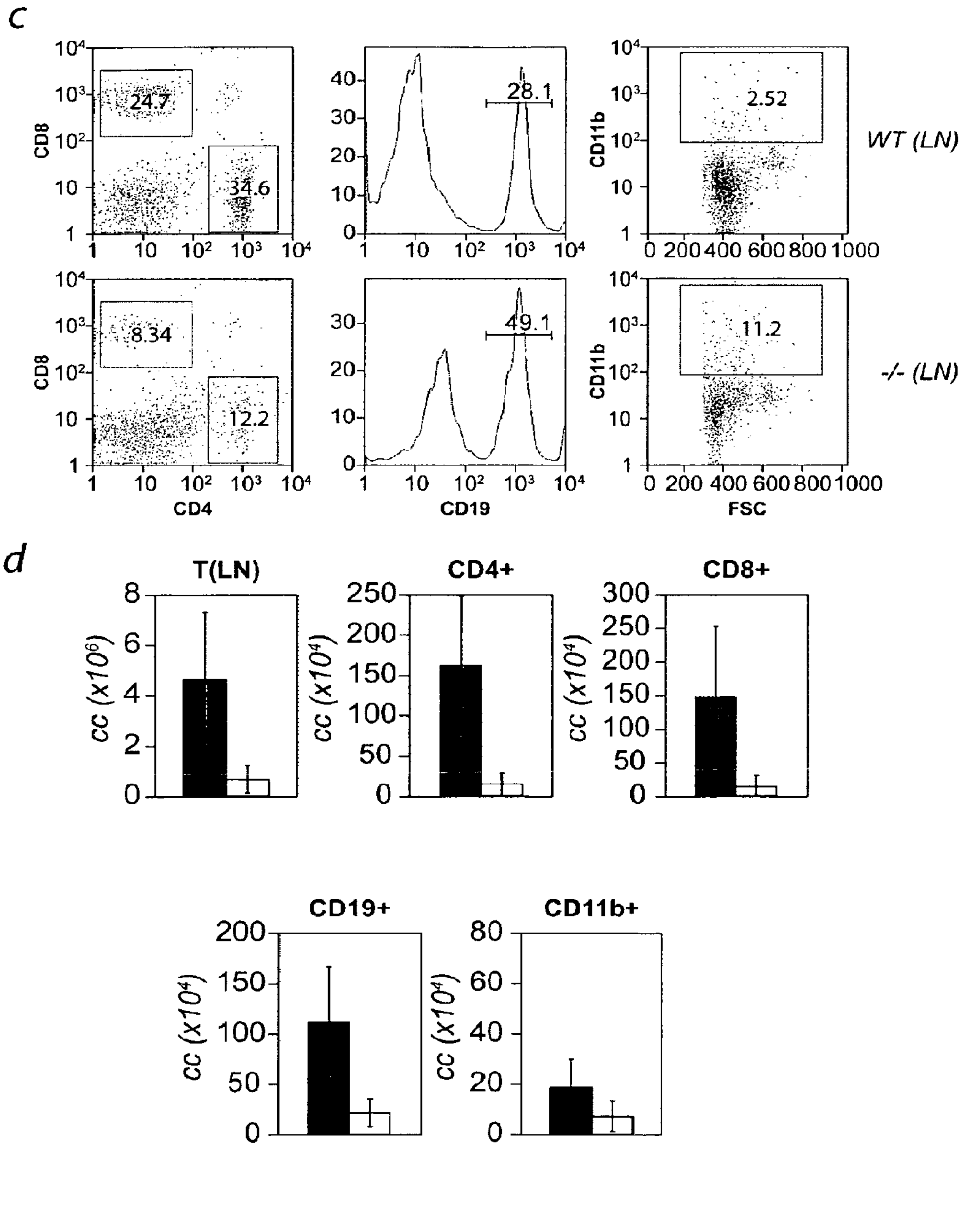
Figure 4:
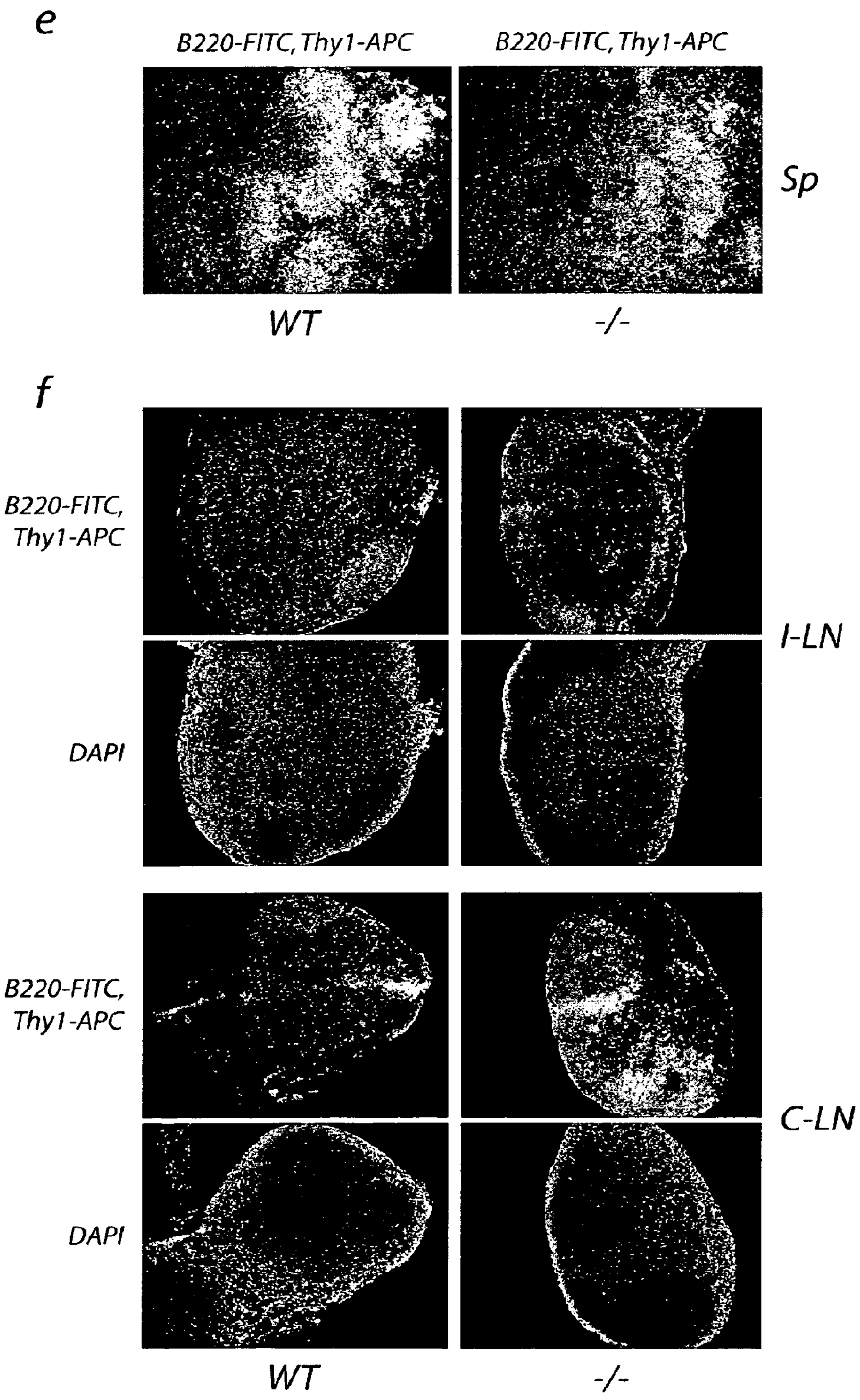

FIG. 4: Peripheral lymphocyte populations in WT and coronin 1 deficient mice.

Cell suspensions of spleen (Sp) or inguinal lymph nodes (LN) of 6 weeks old homozygous (−/−) or wild type (WT) coronin 1 knock-out mice were analyzed by flow cytometry using antibodies directed against the indicated leukocyte markers. FSC: Forward scatter. Cells were counted using a Neubauer chamber. Lymphocyte specific cell numbers were calculated by referring the percentage of a certain cell type (determined by flow cytometry) to the total cell counts (a) Representative flow cytometry profiles of spleen cell suspensions (b) Total (T) and lymphocyte specific spleen cell counts. Filled bars: wild type, open bars: knock-out. Data are means+/−SD of 5 animals (n=5).

(c) Representative flow cytometry profiles of inguinal lymph node cell suspensions.

(d) Total and lymphocyte specific inguinal lymph node cell counts. Filled bars: wild type, open bars: knock-out. Data are means+/−SD of 5 animals (n=5).

(e,f) Spleen (e) or inguinal (I-LN) or cervical (C-LN) lymph nodes (f) from WT or coronin 1 deficient (−/−) mice were prepared for histology and stained for the markers indicated as described in the examples. Magnification: 10×.

Figure 5:
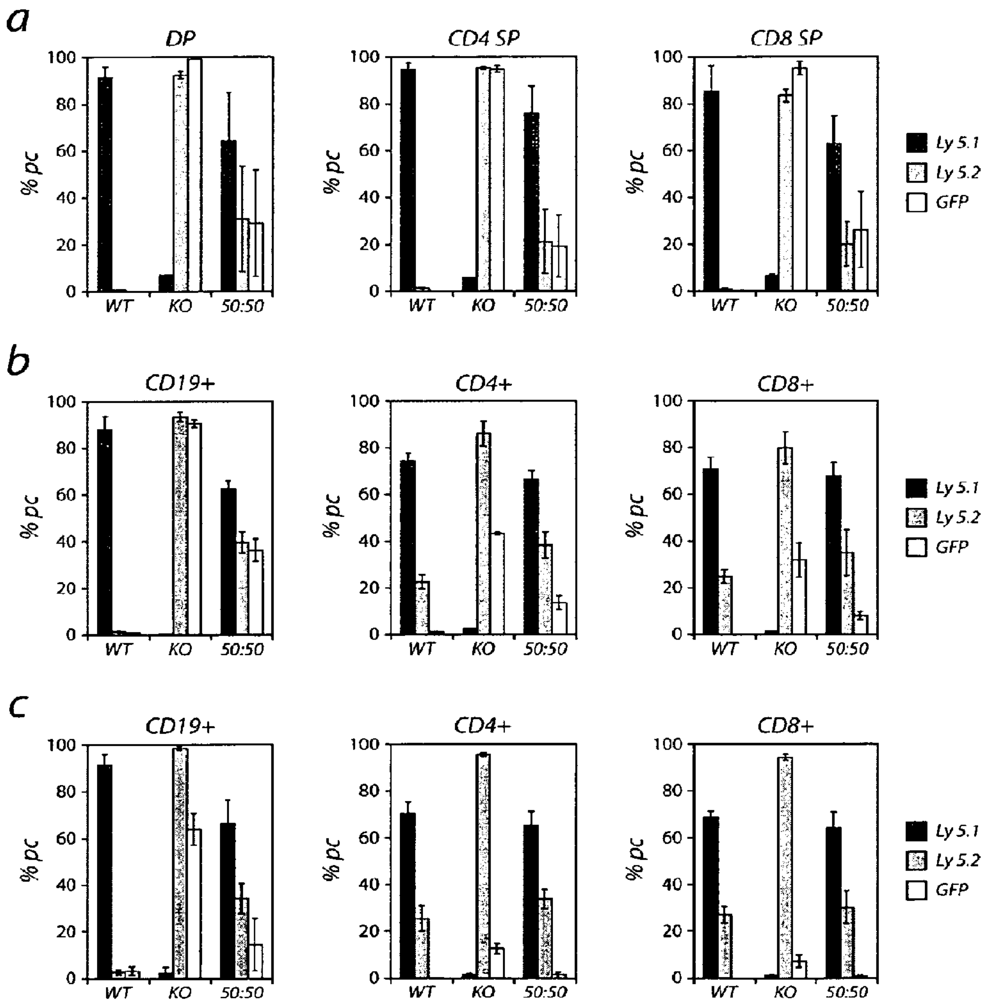
Figure 5:
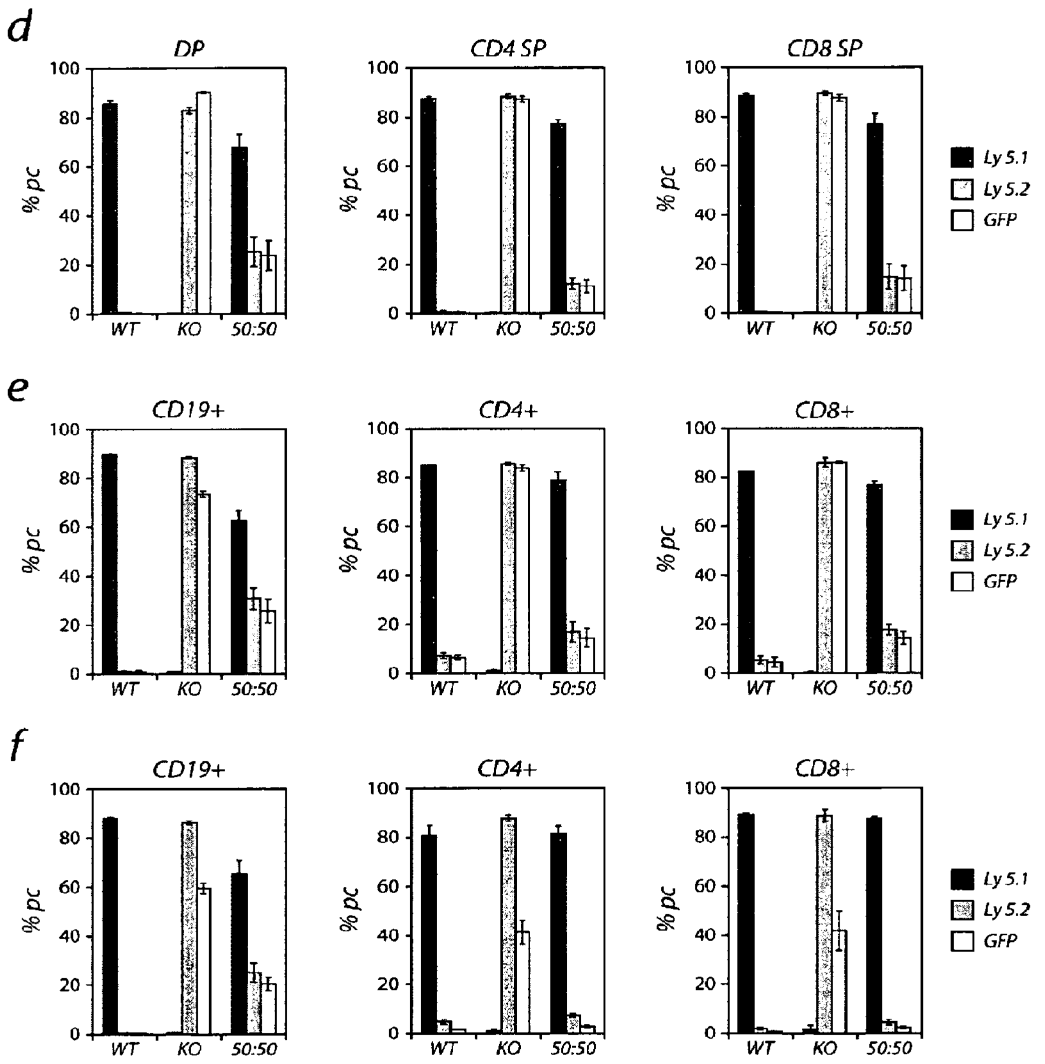

FIG. 5: Bone marrow transplantations

Sub-lethally irradiated recipient mice of wild type (a-c) or coronin $1^{-/-}$ (d-f) origin received either a 1:1 mixture of WT ($Ly5.1^{+}$) and coronin $1^{-/-}$ ($Ly5.2^{+}$) bone marrow cells (50:50) or bone marrow cells of either origin only (WT and KO). Single cell suspensions were analyzed by FACS for Ly5.1, Ly5.2 and GFP expression. The percentage of Ly5.1, Ly5.2 and GFP positive cells within gates identifying specific lymphocyte subsets was determined. Depicted are means+/−SD of three mice in each group (for d-f, in the case of WT 2 animals were used). Reconstitution of thymus (a,d), spleen (b,e) and lymph nodes (c,f). DP: CD4 and CD8 double positive thymocytes. SP: CD4 or CD8 single positive thymocytes. % pc: % positive cells.

Figure 6:
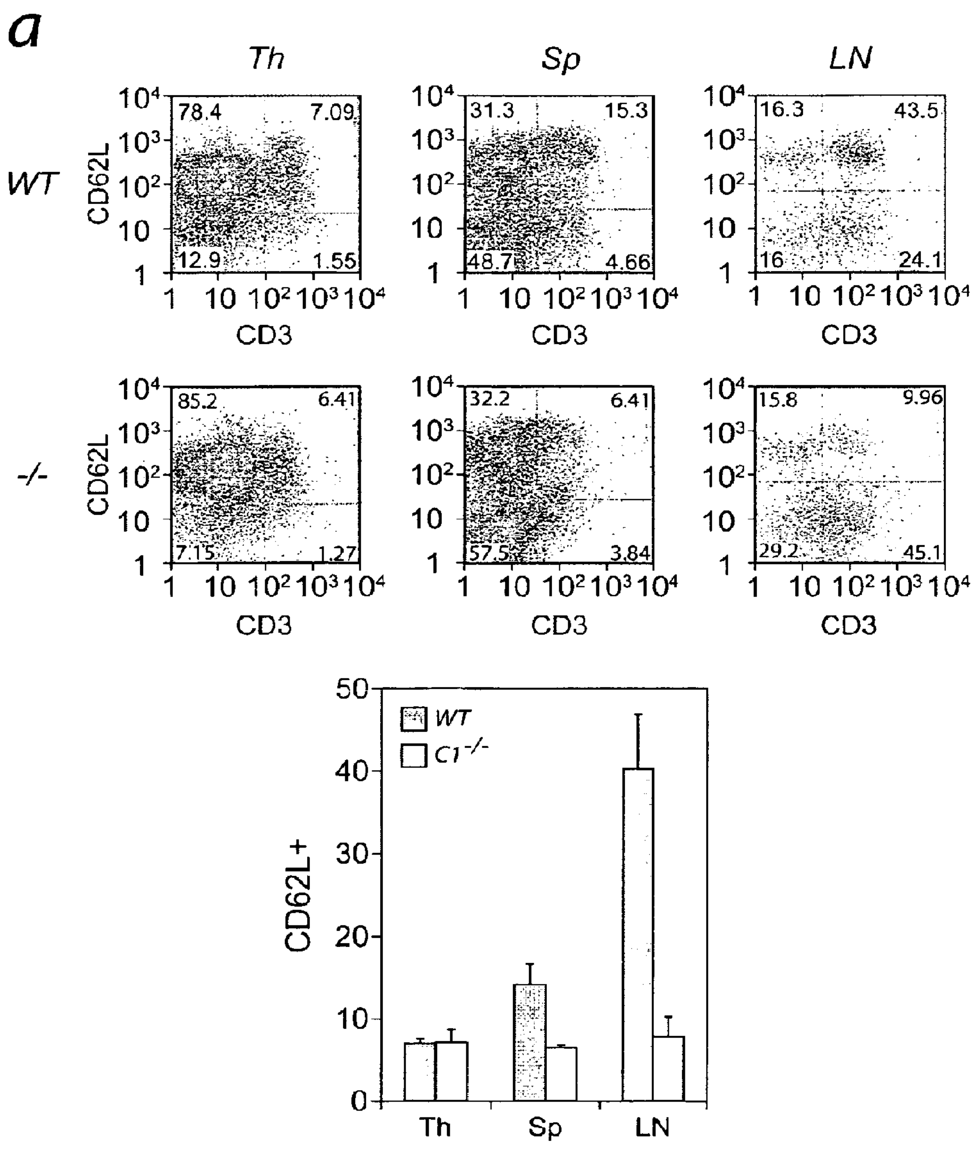
Figure 6:
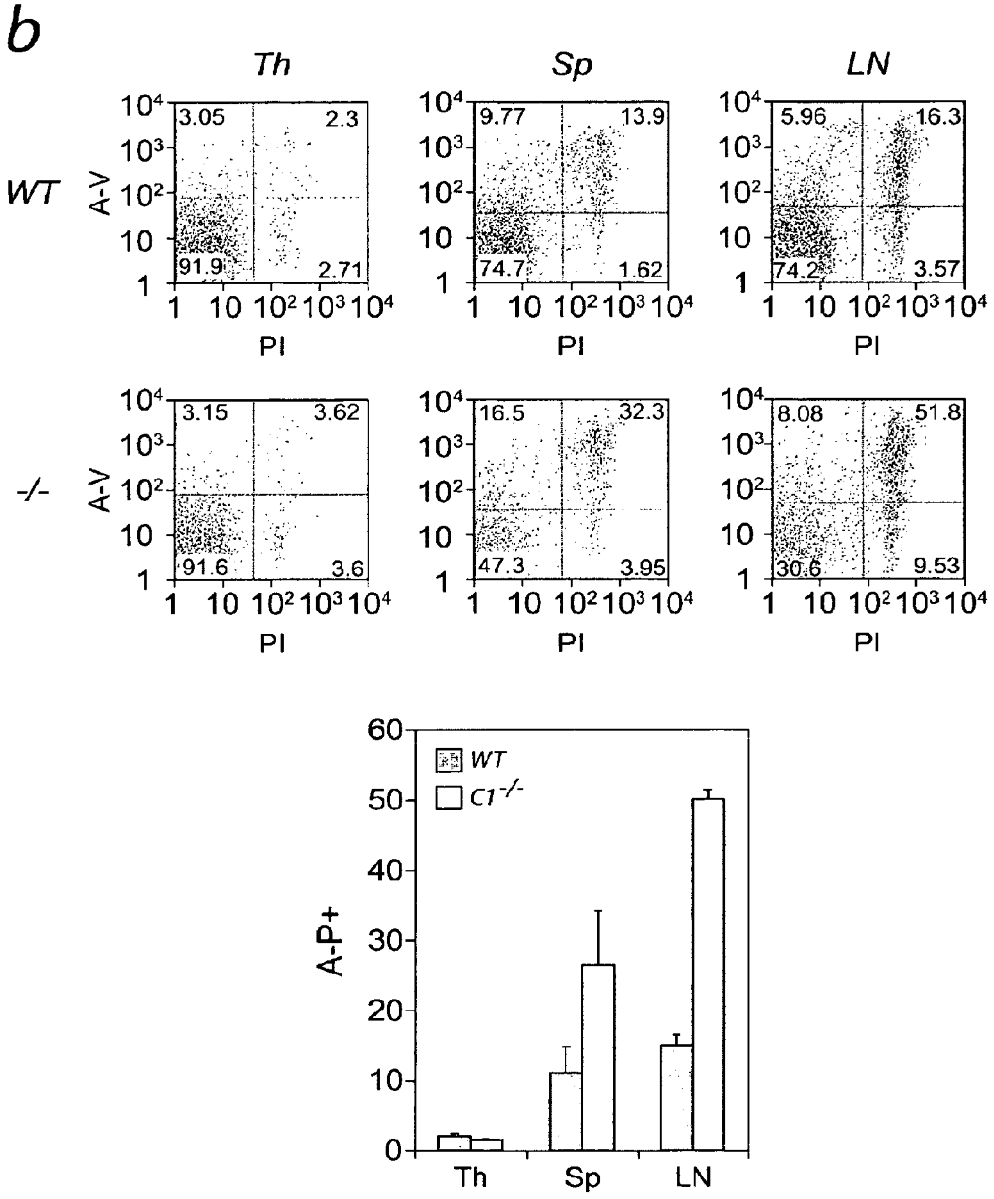

FIG. 6: Homing and apoptosis of T cells in the absence of coronin 1

(a) Cells were isolated from thymus (Th), spleen (Sp) and lymph nodes (LN) of wild type (WT) or coronin $1^{-/-}$ (−/−, $C1^{-/-}$ mice and stained for CD3 and CD62L. Right panel: percentages of CD62L positive CD3+ cells. Shown is the mean(+/−SD) from 3 mice. (b) Cells were isolated from thymus, spleen and lymph nodes of wild type (WT) or coronin 1−/− (−/−) mice and stained for CD3 and incubated with annexin V-APC and PI. Shown are representative dot plots of $CD3^{+}$ cells analyzed for annexin V and PI. Right panel: percentages of Annexin V positive cells (AV-P). Shown is the mean(+/−SD) from 2 mice.

Figure 7:
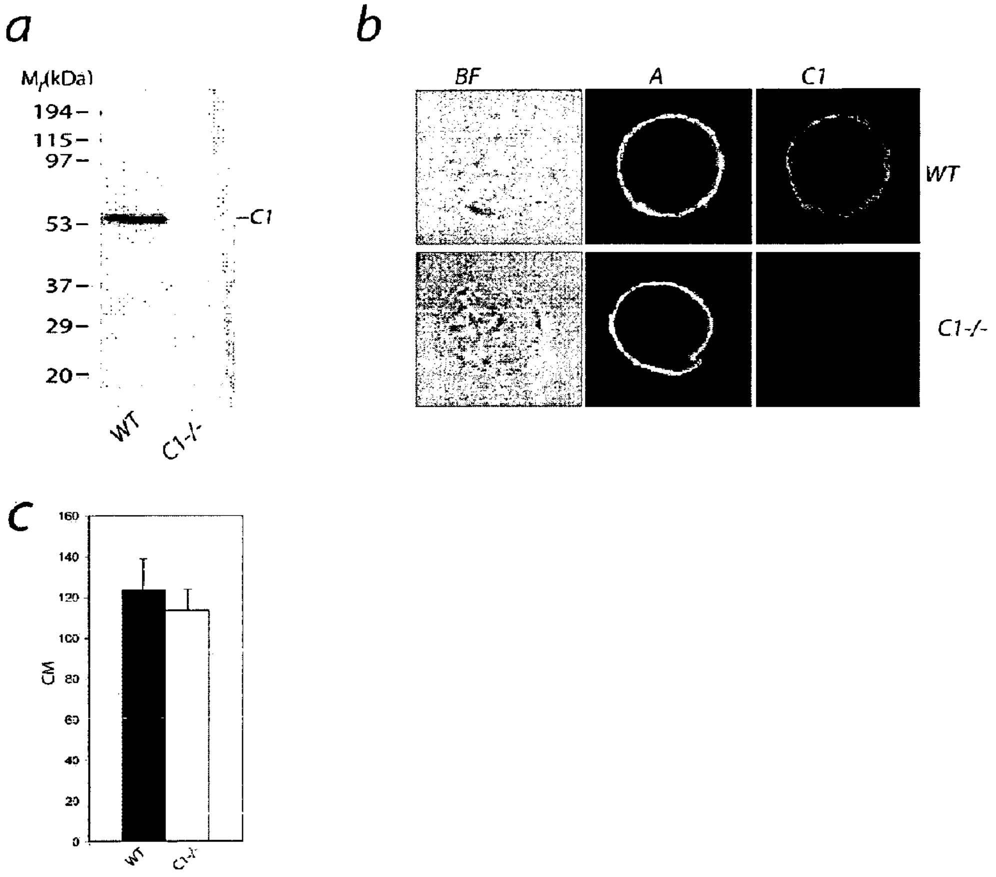

FIG. 7: Phenotype of macrophages in the presence and absence of coronin 1

(a) Bone marrow derived macrophages from wild type (WT) or coronin 1 deficient (C1−/−) mice were lysed in SDS-sample buffer and proteins separated by SDS-PAGE followed by immunoblotting for coronin 1 (C1) and visualization by enhanced chemoluminescence.

(b) Wild type (WT) or coronin 1 deficient (C1−/−) bone marrow derived macrophages were seeded on coverslips, fixed and stained for actin (A) and coronin 1 (C1) primary antibodies followed by Alexa fluor488 and Alexa fluor568 conjugated secondary antibodies, respectively. BF=bright field.

(c) Bone marrow derived macrophages from wild type (WT) or coronin 1 deficient (C1−/−) mice were laid on the top of the migration chamber and allowed to migrate towards the bottom half containing human serum activated zymosan. After 4 h of incubation filters were excised and stained with propidium iodide. Bacteria were counted using fluorescence microscopy. For quantitation, ~125 cells were counted in triplicates. CM=number of cells migrated per field. Results are expressed as mean+/−SD and are a representative of at least two independent experiments.

Figure 8:
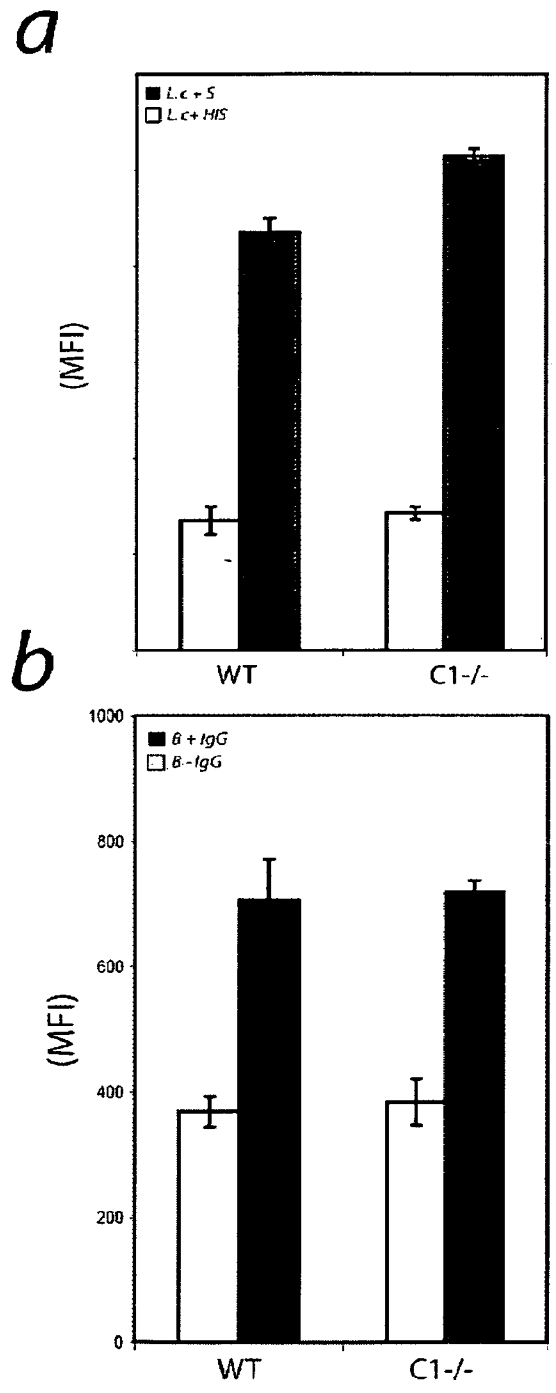

FIG. 8: Phagocytosis in the presence and absence of coronin 1

Flow cytometric analysis of receptor mediated phagocytosis by bone marrow derived macrophages isolated from homozygous coronin 1 knock-out (C1−/−) mice or wildtype (WT) littermates.

(a) To study complement receptor 3 (CR3) mediated uptake adherent macrophages are incubated with GFP expressing *Lactobacillus casei* (L.c) that have either been treated with fresh (S) or heat inactivated human serum (HIS, as control for background uptake). After internalization for 30 min at 37° C. the cells were washed to remove adherent bacteria, harvested by scraping and analysed by flow cytometry. Rate of uptake is determined as the increase in fluorescence as expressed by the median fluorescence intensity (MFI).

(b) Fc receptor-mediated uptake is analysed by incubating adherent macrophages with fluorescent polystyrene beads (B) that have either been coated with IgG or not (as control for background uptake). Flow cytometric analysis of Fc receptor mediated phagocytosis was performed as described for CR3-mediated uptake.

Figure 9:
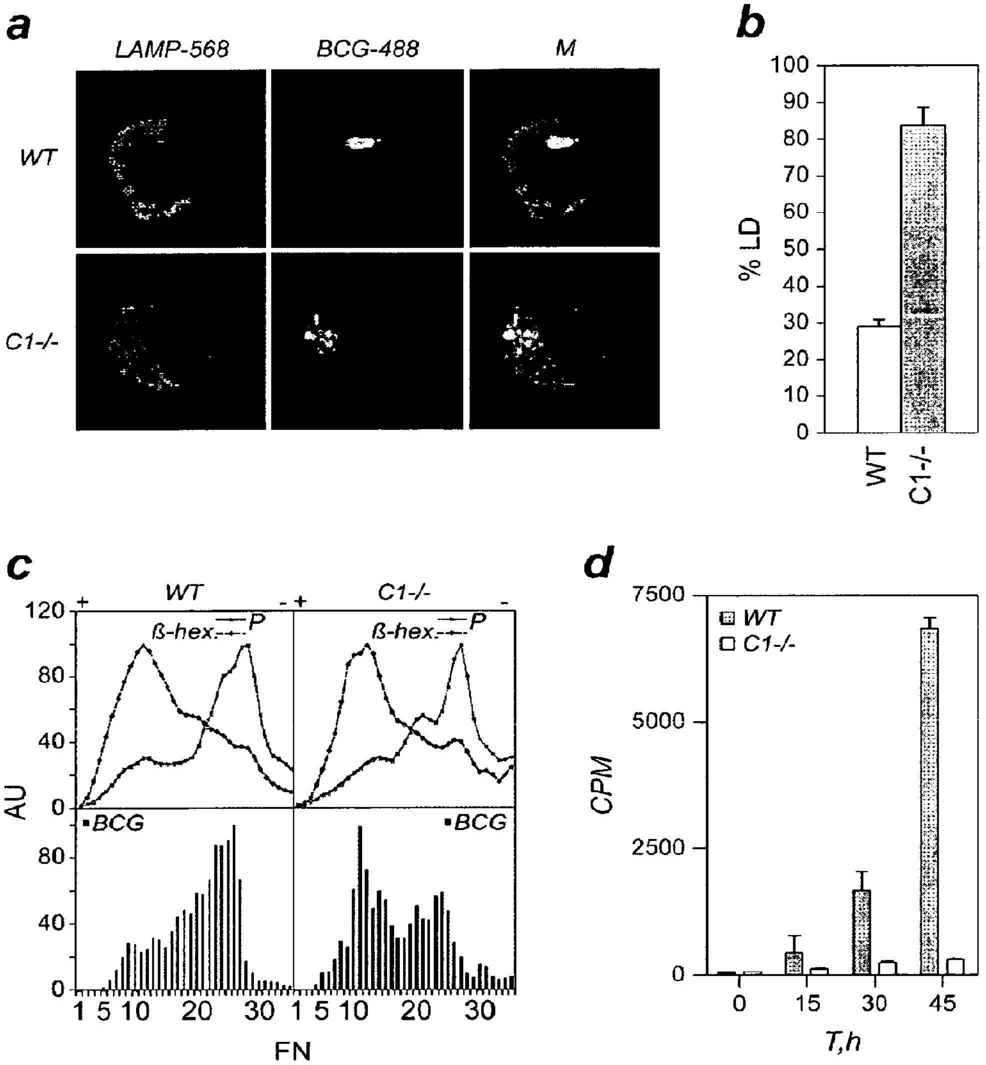

FIG. 9: Trafficking and survival of mycobacteria in wild type and coronin 1 deficient macrophages (a) Intracellular trafficking of mycobacteria. Wild type (WT) or coronin 1 deficient (C1−/−) macrophages were incubated with mycobacteria for 1 h followed by a 3 h chase, methanol fixed and stained for *M. bovis* BCG and LAMP1. M=merge.

(b) For quantitation, cells (n=150) were scored for the co-localization of bacteria with lysosomal marker LAMP1 and represented as percentage co-localization with SD+/− values from at least three independent experiments. LD=lysosomal delivery.

(c) Macrophages from wild type (WT) or coronin 1 deficient C1−/−) mice were incubated for 3 h with mycobacteria, homogenized, and subjected to organelle electrophoresis. The distribution of organelle-specific markers and the amount of bacteria per fraction were determined as described in the Examples. AU=arbitrary units, FN=fraction number, P=protein, β-hex.=β-hexidin, BCG=*M. bovis* BCG.

(d) Mycobacterial survival. Wild type (WT) or coronin 1 deficient (C1−/−) macrophages were seeded per well in a 96 well plate and incubated with mycobacteria for 1 h and chased for the indicated times (T in hours). Mycobacterial viability was analyzed as described in the Examples. Error bars shown are from data derived from triplicates. Data shown is representative of at least three independent experiments. Time given in hours.

Figure 10:
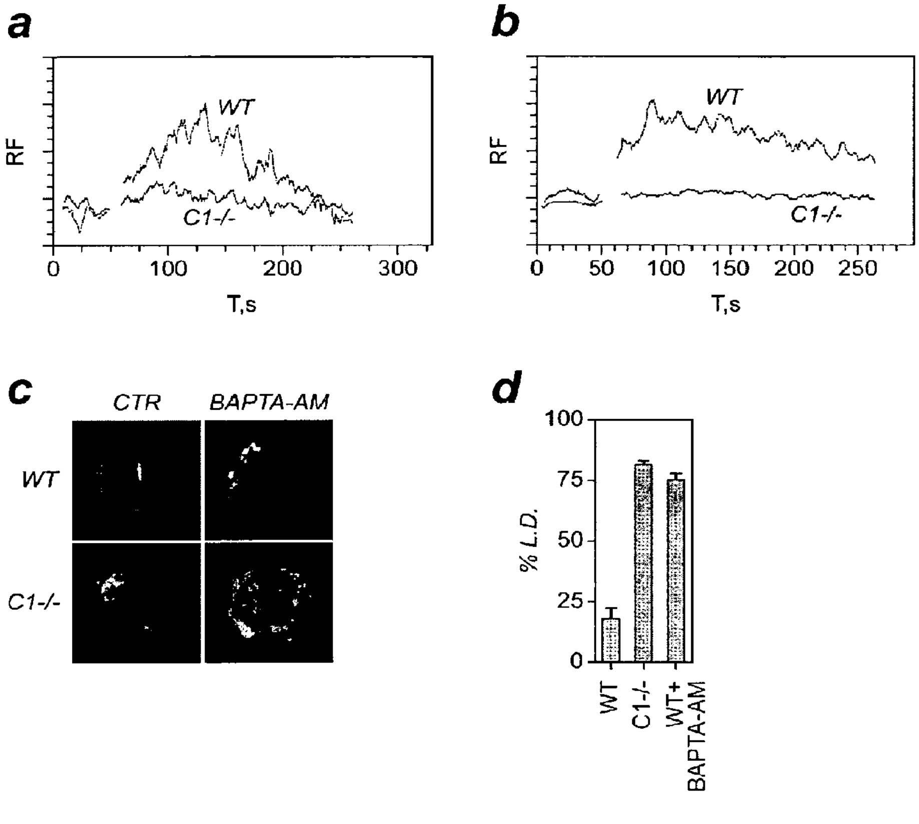
Figure 10:
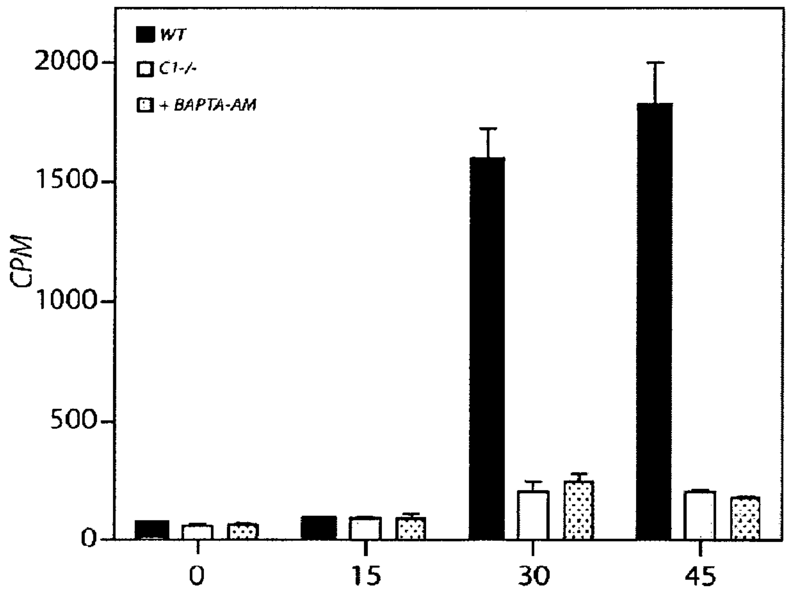
Figure 10:
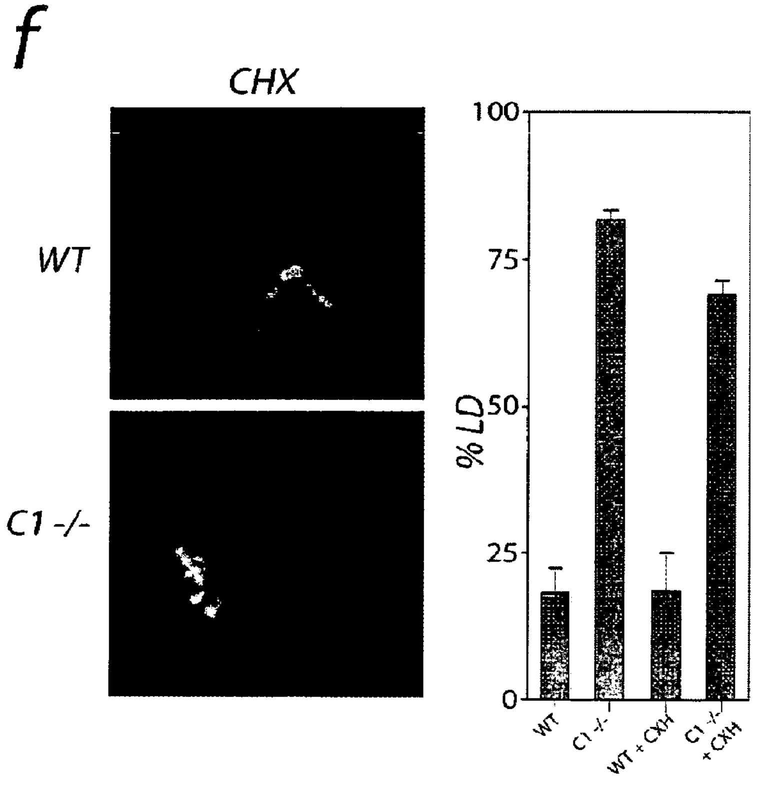
Figure 10:
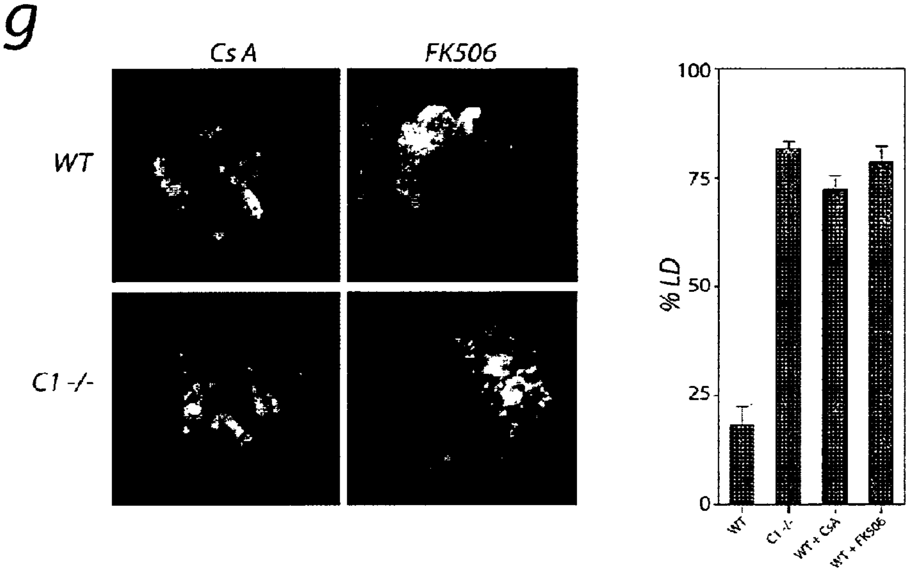
Figure 10:
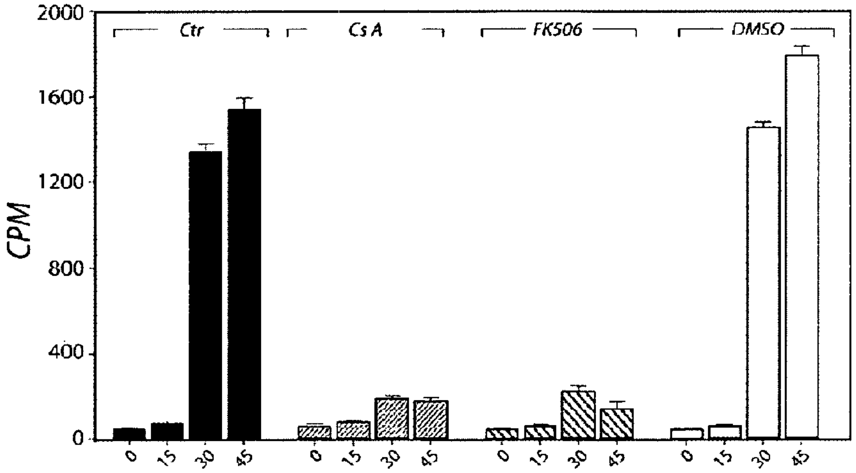

FIG. 10: Intracellular transport and survival of mycobacteria in the absence and presence of calcineurin inhibitors (a,b) Bone marrow derived macrophages ($10\times10^6$ cells) from wild type (WT) or coronin 1 deficient (C1−/−) mice were loaded with calcium specific fluophore Fluo3 as described in the Examples and stimulated with either ionomycin (a) or *M. bovis* BCG (b; 1 OD stock in Ringers solution) at 50 seconds. The fluorescence emission was monitored in channel FL-1 and is plotted against time in seconds (T,s). RF=relative fluorescence. The data shown is representative of at least three independent experiments. Upper curve: Wild type mice. Lower curve: coronin 1 deficient mice.

(c) Bone marrow derived macrophages from both wild type (WT) or coronin 1 deficient (C1−/−) mice were allowed to adhere to slides in the presence of BAPTA-AM and infected with *M. bovis* BCG for 1 h. The cells were chased for 3 h at the end of which they were fixed and stained for mycobacteria and LAMP1 followed by anti-rabbit Alex fluor 488 and anti-rat Alexa fluor 568 conjugated secondary antibodies, respectively.

(d) For quantitation, cells (n=50) were scored for the co-localization of bacteria with LAMP1 and represented as percentage co-localization with SD+/− values from three independent experiments. L.D.=lysosomal delivery.

(e) Survival of mycobacteria within wild type (WT) or coronin 1 deficient (C1−/−) macrophages in the presence of BAPTA-AM. Macrophages were infected as described in the legend to FIG. 9 and were chased for the times (hours) indicated. Survival of the bacteria was analyzed as described in the Examples. The data show representative results obtained from at least three independent experiments.

(f) Bone marrow derived macrophages from wild type (WT) or coronin 1 deficient (C1−/−) mice were infected with mycobacteria in the presence or absence of cycloheximide (CHX) (75 μg/ml) and chased for 3 h at the end of which the cells were fixed with methanol and stained for mycobacteria and LAMP1 as described in panel (c). For quantitation, cells (n=50) were scored for the co-localization of bacteria with lysosomal marker LAMP1 and represented as percentage co-localization with SD+/− values from three independent experiments. LD=lysosomal delivery.

(g) Wild type (WT) or coronin 1 deficient (C1−/−) bone marrow derived macrophages were infected with *M. bovis* BCG in the presence of cyclosporin A (CsA, 0.1 μM) or FK506 (0.5 μM) and chased for 3 h at the end of which the cells were methanol fixed and stained for mycobacteria and LAMP1 as described in panel (c). For quantitation, cells (n=50) were scored for the co-localization of bacteria with lysosomal marker LAMP1 and represented as percentage co-localization with SD+/− values from three independent experiments. LD=lysosomal delivery.

(h) Viability of mycobacteria within wild type bone marrow derived macrophages in the presence of cyclosporin A (CsA) and FK506. Macrophages were infected as described in the legend to FIG. 9 and chased for the times indicated (hours). Survival of the bacteria was analyzed as described in the Examples. The data show representative results obtained from at least three independent experiments.

Figure 11:
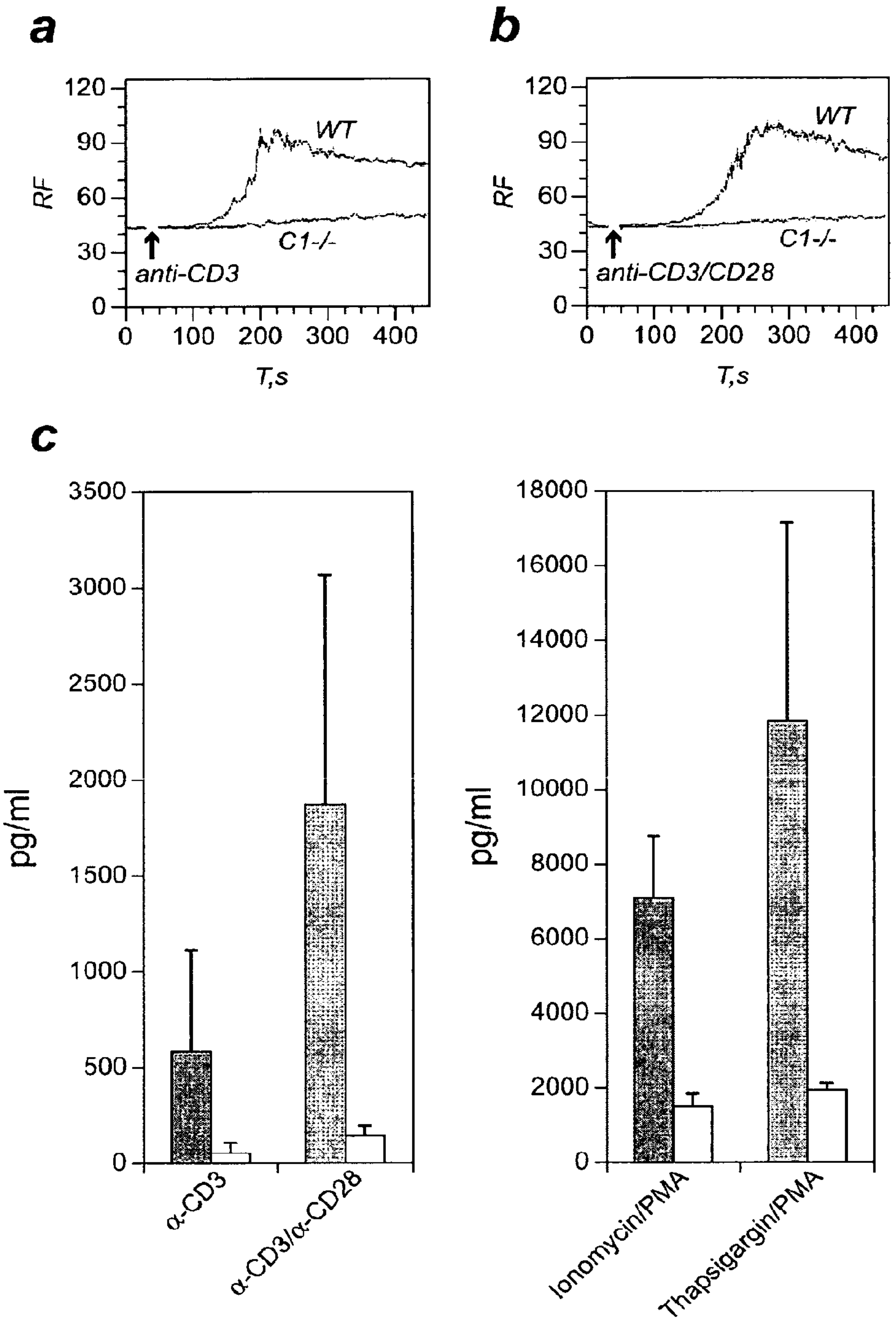

FIG. 11: T cell activation in wild type and coronin 1 deficient T cells.

(a,b) Calcium mobilization upon CD3 (a) or CD3/CD28 (b) stimulation was measured in splenic T-cells by Indo-1 fluorescence and is displayed as the FL4/FL5 ratio (Relative Calcium Flux, RF). Total splenocytes were loaded with Indo-1 by incubation with Indo-1 AM, and labeled with anti-CD19-PE and anti-CD11b-PE. Only PE negative cells were analyzed for calcium mobilization upon CD3/CD28 stimulation. The arrows indicate the time of addition of the stimulus. The relative calcium flux is expressed as the FL4/FL5 ratio. Shown is one representative out of 3 experiments using independent pairs of mice. Less than 5% of the gated cells stained positive for annexin V (data not shown).

(c) Interleukin-2 (in pg/ml) production by wild type (filled bars) and coronin 1−/− (open bars) spleen suspensions following the indicated stimulation.

DETAILED DESCRIPTION OF THE INVENTION

The present invention relates to a method of treating mycobacterial infections, autoimmune disorders, lymphoproliferative disorders and induction of immunosuppression following transplantation comprising administering coronin 1 or a modulator of coronin 1, and the use of coronin 1 and coronin 1 modulators in said treatment and in the manufacture of medicaments for treating mycobacterial infections, autoimmune disorders, lymphoproliferative disorders and induction of immunosuppression following transplantation.

Coronin 1 modulators are compounds which downregulate the overall coronin 1 levels within a T cell. More particularly, coronin 1 modulators are compounds which inhibit the production of coronin 1 or the formation of active coronin 1 from a coronin 1 precursor, partly or entirely inactivate coronin 1, inhibit concentration of coronin 1 at the immunological T cell synapse, or inhibit the coronin 1 mediated signaling pathway downstream of the T cell receptor.

Coronin 1 modulators are furthermore coronin 1 agonists, which reinforce coronin 1 concentration at the site of T cell stimulation.

Coronin 1 production can be inhibited by anti-sense oligodeoxynucleotides, siRNAs (small interfering RNA) or shRNA (small hairpin RNA). Prevention of the formation of active coronin 1 can be achieved by targeting coronin 1 precursors. A further example of a compound considered as coronin 1 modulator according to the invention is a binding composition which specifically and/or selectively binds coronin 1, and which neutralizes coronin 1, i.e. a compound comprising antigen binding sites of anti-coronin 1 Fabs.

Targeting of coronin 1 can be achieved by the administration of neutralizing antibodies to coronin 1 or by the administration of proteins or synthetic compounds, which bind coronin 1, and thereby prevent its natural function in T cells. Alternatively, peptides comprising parts of coronin 1 can be used as coronin 1 modulators according to the invention, for example the C-terminal coiled coil, the different segments that make up the seven-bladed propeller domain or the linker domain (J. Gatfield et al., Mol Biol Cell 2005, 16, 2786). Further examples of coronin 1 modulators according to the invention are compounds which by binding to coronin 1 interfere with immunological T cell stimulation.

Modulation of coronin 1 can also be accomplished by gene therapy, for example by using vectors harboring cDNA, which encodes for proteins binding coronin 1 genes, cDNA coding for coronin 1 parts, for example the C-terminal coiled coil or the WD repeat domain of coronin 1, or cDNA related to genes involved in the activation or inactivation of coronin 1. Such cDNA and vectors harboring cDNA are likewise considered coronin 1 modulators according to the invention.

Anti-coronin 1 antibodies considered to be coronin 1 modulators according to this invention may be obtained as follows:

Polyclonal antisera are raised against KLH-coupled peptides spanning different regions of the coronin 1 sequence in New Zealand white rabbits, and antibodies are affinity purified by affinity chromatography using the immunizing peptides as ligands. For the generation of antiserum against recombinantly expressed coronin 1, the coding sequence (full sequence or parts of the sequence) of coronin 1 can be fused to the GST sequence in the pGEX-4T-1 expression vector, and the fusion protein can be expressed in *E. coli*, and purified. Both native and SDS-denatured recombinant coronin 1 can be used for immunization of rabbits to obtain an anti-coronin 1 antiserum.

Monoclonal antibodies can be generated by immunizing rats (for example Wistar) with peptides (15-20-mer) and fusion of the spleen and lymph nodes, for example, with SP2/0 myeloma cells. Alternatively, monoclonal antibodies can be prepared in mice (for example Balb/c) following immunization and fusion of spleen and lymph nodes with the appropriate myeloma cell lines, such as P3X63-Ag8.653 (Balb/c).

Both poly- and monoclonal anti-coronin peptides can be generated against recombinant protein, fragments thereof or peptide sequences (15-20-mers) produced as described below.

Antibodies (monoclonal and/or polyclonal) are purified and Fab fragments are prepared by partial fragmentation, for example by cleavage with papain or pepsin, which produces two Fab fragments or F(ab)2 fragments, respectively. Also, the DNA that encodes the binding portion of monoclonal mouse antibodies can be cloned and merged with human antibody producing DNA. Mammalian cell cultures can be used to express this DNA and produce such humanized antibodies. Another approach involves mice genetically engineered for the production of such antibodies.

Preferred coronin 1 peptides useful as coronin 1 modulators according to the invention are the following peptides derived from human coronin 1:

Amino acid residues 400-416, representing the domain interacting with the cytoskeleton:

```
                                        (SEQ ID NO: 1)
KSRELRVNRGLDTGRRR
```

Amino acid residues 430-461 that constitute the coiled coil domain:

```
                                        (SEQ ID NO: 2)
VSRLEEEMRKLQATVQELQKRLDRLEETVQAK

                                        (SEQ ID NO: 3)
N-terminal domain: MSRQVVRSSKFRHVFGQPAKADQCYE
```

Peptides spanning the WD repeats (WD repeats are characterized by a 30 to 40 amino acid residue segment bordered by Gly-His (GH) and Trp-Asp (WD) di-peptide residues):

```
                                        (SEQ ID NO: 4)
VCGHTAPVLDIAWCPHNDNVIASGSEDCTVMVWE

                                        (SEQ ID NO: 5)
LEGHTKRVGIVAWHTTAQNVLLSAGCDNVIMVWD

                                        (SEQ ID NO: 6)
PEVHPDTIYSVDWSRDGGLICTSCRDKRVRIIE

                                        (SEQ ID NO: 7)
DRPHEGTRPVRAVFVSEGKILTTGFSRMSERQVALWD

                                        (SEQ ID NO: 8)
PLSLQELDTSSGVLLPFFDPDTNIVYLCGKGDSSIRYF
```

Peptides can be synthesized on an automated peptide synthesizer, such as the Abimed AMS 422 Multiple Peptide Synthesizer, using, for example, the standard Fmoc chemistry on solid supports (E. Atherton and R. C. Sheppard, Solid Phase peptide synthesis: a practical approach. IRL Press, Oxford, England, 1989).

Alternatively, peptide fragments such as those described above can be cloned into the appropriate expression vectors with or without a tag to allow affinity purification, and expressed in mammalian cell culture systems.

Coronin 1 phospho-peptides are likewise considered coronin 1 modulators according to the invention. Phospho-peptides can be synthesized as described above, by incorporating the appropriate phospho-amino acids instead of the non-phosphorylated amino acid residues during synthesis. For the synthesis of the phospho-peptides, phospho-amino acids derived from serine, threonine or tyrosine, preferably from serine or threonine, are used and 15- or 20-mers prepared. Preferred are phospho-peptides of the sequences listed above as coronin 1 peptides, wherein one or more, for example one, two, three, four or five, serine and/or threonine residues are phosphorylated.

Further considered as coronin 1 modulators are suitable siRNA and shRNA. Sequences that will be used to generate siRNA or shRNA in order to block coronin 1 expression are based on the following target sequences, as designed according to the rules as, for example, described in C. Sachse et al., Methods Enzymol. 2005, 392, 242-277:

Target sequence AAGTTCCGCCACGTGTTTGGA (SEQ ID NO: 9)
Sense strand siRNA: GUUCCGCCACGUGUUUGGA (SEQ ID NO: 10)
Antisense strand siRNA: UCCAAACACGUGGCGGAAC Target sequence AAGGCCGACCAGTGCTATGAA (SEQ ID NO: 11)
Sense strand siRNA: GGCCGACCAGUGCUAUGAA (SEQ ID NO: 12)
Antisense strand siRNA: UUCAUAGCACUGGUCGGCC Target sequence AAGATGTGCGCGTCTCACAGA (SEQ ID NO: 13)
Sense strand siRNA: GAUGUGCGCGUCUCACAGA (SEQ ID NO: 14)
Antisense strand siRNA: UCUGUGAGACGCGCACAUC Target sequence AACCCTAAGTTTGTGGCCCTG (SEQ ID NO: 15)
Sense strand siRNA: CCCUAAGUUUGUGGCCCUG (SEQ ID NO: 16)
Antisense strand siRNA: CAGGGCCACAAACUUAGGG Target sequence AAGTTTGTGGCCCTGATCTGT (SEQ ID NO: 17)
Sense strand siRNA: GUUUGUGGCCCUGAUCUGU (SEQ ID NO: 18)
Antisense strand siRNA: ACAGAUCAGGGCCACAAAC siRNA duplexes are prepared by standard chemistry. Alternatively, such sequences may be cloned into suitable vectors such as the pSUPER system or adeno- and lenti viral based systems to generate short hairpin RNA (shRNA) that is subsequently processed into active siRNA (G. D. Fewell and K. Schmitt, Drug Discov. Today 2006, 11, 975-982).

One aspect of the invention relates to a method of treating mycobacterial infections, autoimmune disorders, lymphoproliferative disorders and induction of immunosuppression following transplantation comprising administering coronin 1 or coronin 1 modulators as defined hereinbefore in a quantity effective against mycobacterial infections, autoimmune disorders, lymphoproliferative disorders and induction of immunosuppression to a mammal in need thereof, for example to a human requiring such treatment. The treatment may be for prophylactic or therapeutic purposes. For the administration, coronin 1 or the coronin 1 modulator is preferably in the form of a pharmaceutical preparation comprising the coronin 1 or the coronin 1 modulator in chemically pure form and optionally a pharmaceutically acceptable carrier and optionally adjuvants. Coronin 1 or the coronin 1 modulator is used in an amount effective against mycobacterial infections, autoimmune and lymphoproliferative disorders. The dosage of the active ingredient depends upon the species, its age, weight, and individual condition, the individual pharmacokinetic data, the mode of administration, and whether the administration is for prophylactic or therapeutic purposes. In the case of an individual having a bodyweight of about 70 kg the daily dose administered is from approximately 1 mg to approximately 500 mg, preferably from approximately 10 mg to approximately 100 mg, of coronin 1 or a coronin 1 modulator.

In particular, the compounds of the invention are useful in the treatment and/or prevention of diseases or disorders mediated by lymphocyte interactions, e.g. in transplantation, such as acute or chronic rejection of cell, tissue or organ allo- or xenografts or delayed graft function, graft versus host disease, autoimmune diseases, e.g. rheumatoid arthritis, systemic lupus erythematosus, Hashimoto's thyroidis, multiple sclerosis, myasthenia gravis, diabetes type I or II and the disorders associated therewith, vasculitis, pernicious anemia, Sjoegren syndrome, uveitis, psoriasis, Graves ophthalmopathy, alopecia areata and others, allergic diseases, e.g. allergic asthma, atopic dermatitis, allergic rhinitis/conjuctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatitises, seborrhoeic dermatitis, cutaneous manifestations of immunologically-mediated disorders, inflammatory eye diseases, keratoconjuctivitis, myocarditis or hepatitis, ischemia/reperfusion injury, e.g. myocardial infarction, stroke, gut ischemia, renal failure or hemorrhage shock, traumatic shock, cancer, e.g. T cell lymphomas or T cell leukamias, infectious diseases, e.g. toxic shock (e.g. superantigen induced), septic shock, adult respiratory distress syndrome or viral infections, e.g. AIDS, viral hepatitis or chronic bacterial infection, e.g. tuberculosis. Examples of cell, tissue or solid organ transplants include e.g. pancreatic islets, stem cells, bone marrow, corneal tissue, neuronal tissue, heart, lung, combined heart and lung, kidney, liver, bowel, pancreas, trachea or oesophagus. Furthermore, the compounds of the invention are useful in the treatment and/or prevention of mycobacterial infections. Mycobacterial infections include tuberculosis, caused by *Mycobacterium tuberculosis*, leprosy, caused by *Mycobacterium leprae*, as well as infections caused by *Mycobacterium marinum, Mycobacterium bovis, Mycobacterium avium, Mycobacterium intracellulare, Mycobacterium kansasii, Mycobacterium malmoense, Mycobacterium simiae, Mycobacterium szulgai, Mycobacterium xenopi, Mycobacterium scrofulaceum*—associated with lymphadenitis, *Mycobacterium abscessus, Mycobacterium chelonae, Mycobacterium haemophilum*, and *Mycobacterium ulcerans.*

Pharmaceutical compositions for enteral administration, such as nasal, buccal, rectal or, especially, oral administration, and for parenteral administration, such as subcutaneous, intravenous, or intramuscular are especially preferred. The pharmaceutical compositions comprise from approximately 1% to approximately 95% active ingredient, preferably from approximately 20% to approximately 90% active ingredient.

For parenteral administration preference is given to the use of solutions of coronin 1 or the coronin 1 modulator, and also suspensions or dispersions, especially isotonic aqueous solutions, dispersions or suspensions which, for example, can be made up shortly before use. The pharmaceutical compositions may be sterilized and/or may comprise excipients, for example preservatives, stabilizers, wetting agents and/or emulsifiers, solubilizers, viscosity-increasing agents, salts for regulating osmotic pressure and/or buffers and are prepared in a manner known per se, for example by means of conventional dissolving and lyophilizing processes.

For oral pharmaceutical preparations suitable carriers are especially fillers, such as sugars, for example lactose, saccharose, mannitol or sorbitol, cellulose preparations and/or calcium phosphates, and also binders, such as starches, cellulose derivatives and/or polyvinylpyrrolidone, and/or, if desired, disintegrators, flow conditioners and lubricants, for example stearic acid or salts thereof and/or polyethylene glycol. Tablet cores can be provided with suitable, optionally enteric, coatings. Dyes or pigments may be added to the tablets or tablet coatings, for example for identification purposes or to indicate different doses of active ingredient. Pharmaceutical compositions for oral administration also include hard capsules consisting of gelatin, and also soft, sealed capsules consisting of gelatin and a plasticizer, such as glycerol or sorbitol. The capsules may contain the active ingredient in the form of granules, or dissolved or suspended in suitable liquid excipients, such as in oils.

Transdermal application is also considered, for example using a transdermal patch, which allows administration over an extended period of time, e.g. from one to twenty days.

Another aspect of the invention relates to the use of coronin 1 or coronin 1 modulators as described hereinbefore in the treatment of autoimmune disorders, lymphoproliferative disorders and induction of immunosuppression following transplantation and in the manufacture of medicaments for treating autoimmune disorders, lymphoproliferative disorders and induction of immunosuppression following transplantation. Such medicaments are manufactured by methods known in the art, especially by conventional mixing, coating, granulating, dissolving or lyophilizing.

Coronin 1 or the coronin 1 modulator can be administered alone or in combination with one or more other therapeutic agents, possible combination therapy taking the form of fixed combinations of coronin 1 or the coronin 1 modulator and one or more other therapeutic agents known in the treatment of mycobacterial infections, autoimmune disorders, lymphoproliferative disorders and induction of immunosuppression following transplantation, the administration being staggered or given independently of one another, or being in the form of a fixed combination.

The invention further relates to a method of screening for a compound effective in the treatment of mycobacterial infections, autoimmune disorders, lymphoproliferative disorders and induction of immunosuppression following transplantation comprising contacting a candidate compound with coronin 1 or a coronin 1 expressing cell, and choosing candidate compounds which selectively modulate activity of coronin 1 or lead to reduced or enhanced expression of coronin 1. The invention further relates to compounds selected by these methods of screening.

Inhibitors of coronin 1 activity are identified by contacting coronin 1 with a candidate compound. A control assay with coronin 1 in the absence of the candidate compound is run in parallel. A decrease in activity in the presence of the candidate compound compared to the level in the absence of the compound indicates that the compound is a coronin 1 inhibitor.

The present invention likewise relates to a method of treating mycobacterial infections, comprising administering calcineurin modulators such as cyclosporin A and tacrolimus (FK506), and the use of calcineurin modulators such as cyclosporin A and tacrolimus (FK506) in said treatment and in the manufacture of medicaments for treating mycobacterial infections.

Concepts and Evidence Behind the Invention

Coronin 1 is important for survival of T lymphocytes in the periphery; in the absence of coronin 1, naïve T cells undergo apoptosis and are fully depleted from secondary lymphoid organs. In contrast, developmental processes in the thymus are not compromised in the absence of coronin 1. Coronin 1 specifically functions in the survival of peripheral T cells without affecting T cell development in the thymus.

The reason for T cells to become deleted from the periphery is because coronin 1 is essential to allow $Ca^{2+}$ signaling following T cell receptor triggering (FIGS. 10*a* and *b*).

The peripheral T cell population is maintained at near constant levels; maintenance of naïve T cells in the periphery is dependent on the appropriate stimulation of T cells through their T cell receptors. Indeed, in hosts that lack peripheral MHC class I or class II expression, T cells are unable to survive because of the absence of TCR-mediated T cell stimulation (J. Kirberg et al., J. Exp. Med. 1997, 186, 1269-1275). Also, induction of T cell receptor deletion results in the disappearance of peripheral T cells (N. Labrecque et al., Immunity 2001, 15, 71-82) showing that T cells need input signals through T cell receptor triggering to support their survival in the periphery.

Triggering of the T cell receptor results in the activation of $Ca^{2+}$ dependent signaling pathways, that in turn activates a diverse array of transcription factors (E. M. Gallo et al., Nat. Immunol. 2006, 7, 25-32). Activation of such $Ca^{2+}$ dependent pathways occurs following influx of $Ca^{2+}$ into the cytosol at two stages. First, T cell receptor triggering stimulates $Ca^{2+}$ release from the intracellular endoplasmic reticulum stores which results in a rapid and transient increase in cytosolic $Ca^{2+}$ concentration (M. M. Winslow et al., Curr. Opin. Immunol. 2003, 15, 299-307). Second, depletion of these intracellular stores results in the opening of plasma membrane $Ca^{2+}$ channels, the so-called store operated channels (SOC) or $Ca^{2+}$ release-activated Ca2+ (CRAC) channels.

In this invention it is shown that coronin 1 controls TCR-dependent cytosolic $Ca^{2+}$ mobilization from intracellular stores and plasma membrane CRAC channels, thereby regulating the survival of naïve T cells in the periphery (FIG. 11). In the absence of coronin 1, $Ca^{2+}$ mobilization does not occur, and, as a consequence, translocation of the T cell specific transcription factor NFAT is not induced resulting in defective interleukin-2 production and T cell death. Coronin 1 is a specific survival factor for peripheral T cells, and, as a consequence, compounds inhibiting or modulating coronin 1 are useful in the treatment of autoimmune disorders, lymphoproliferative disorders and induction of immunosuppression following transplantation. In fact, the most successful current immunosuppressants rely on the abrogation of $Ca^{2+}$ signaling, as exemplified by the successful treatment of autoimmune disorders, lymphoproliferative disorders and induction of immunosuppression following transplantation using cyclosporin A or FK506 (tacrolimus), both of which block NFAT translocation and IL-2 production by inhibiting the activation of the $Ca^{2+}$ dependent phosphatase calcineurin.

Autoimmunity is a disorder that is caused by the presence of predominantly T cells that become activated against self tissue in the peripheral organs (for examples diabetes or multiple sclerosis). Similarly, T cells play a central role in the specific immune response of allograft rejection. Strategies to prevent T cell activation, proliferation or effector function are thus all potentially useful for immunosuppression for the treatment of autoimmunity and transplantation (K. L. Hardinger et al., Pharmacotherapy 2004, 24, 1159-1176).

The presence of T cells and their activation in the peripheral tissues that cause autoimmunity or transplant rejection depend on the production of the essential cytokine interleukin-2 by T cells. Stimulation of the T cell receptor that results in T cell activation and interleukin-2 production occurs through the presentation of self antigens in the case of autoimmune diseases, and foreign antigens in the case of transplant rejection by the molecules of the Major Histocompatibility Complex (MHC).

Triggering of the T cell receptor results, via tyrosine phosphorylation of adaptor molecules, to influx of calcium from intracellular and extracellular stores that is dependent on coronin 1 (FIG. 11). The coronin 1-dependent increase of calcium activates the $Ca^{2+}$ dependent phosphatase calcineurin, that, via dephosphorylation of the T cell transcription factor Nuclear Factor of Activated T cells (NFAT) results in interleukin-2 gene transcription and interleukin-2 production. In the absence of coronin 1, calcium mobilization cannot occur and therefore interleukin-2 is not produced resulting in T cell depletion.

The phenotype of coronin 1–/– mice with respect to the absence of T cells from the periphery is reminiscent of that of mice containing a deletion of genes involved in lymphocyte migration (Y. Fukui et al., Nature 2001, 412, 826-831; M. Matloubian et al., Nature 2004, 427, 355-360). However, the finding that coronin 1–/– mice do not display an aberrant actin or tubulin cytoskeleton nor accumulated single positive T cells in the thymus is inconsistent with such a migration defect. Lymphocyte homing is not compromised which is consistent with the normal acquisition of the lymphocyte homing receptor CD62L on coronin 1 deficient thymocytes.

Rather than functioning in lymphocyte homing and migration, coronin 1 may modulate the strength of signaling downstream of the T cell receptor. This is suggested by the fully normal development within the thymus of coronin 1–/– mice. Also, the increased apoptosis of coronin 1 deficient mice suggests a lack of the appropriate stimulus that is normally required to allow survival of T cells in the periphery (S. Takeda et al., Immunity 1996, 5, 217-228). Interestingly, coronin 1 binds to cellular membranes in a cholesterol-dependent manner (J. Gatfield and J. Pieters, Science 2000, 288, 1647-1650) and its location at the immunological synapse suggest an important function during T cell signaling. While additional mechanisms must exist to differentiate thymus-derived signals from those that T cells receive in the periphery, coronin 1 is important for signal transmission in the periphery only.

Coronin 1 in T Cells

Figure 1:
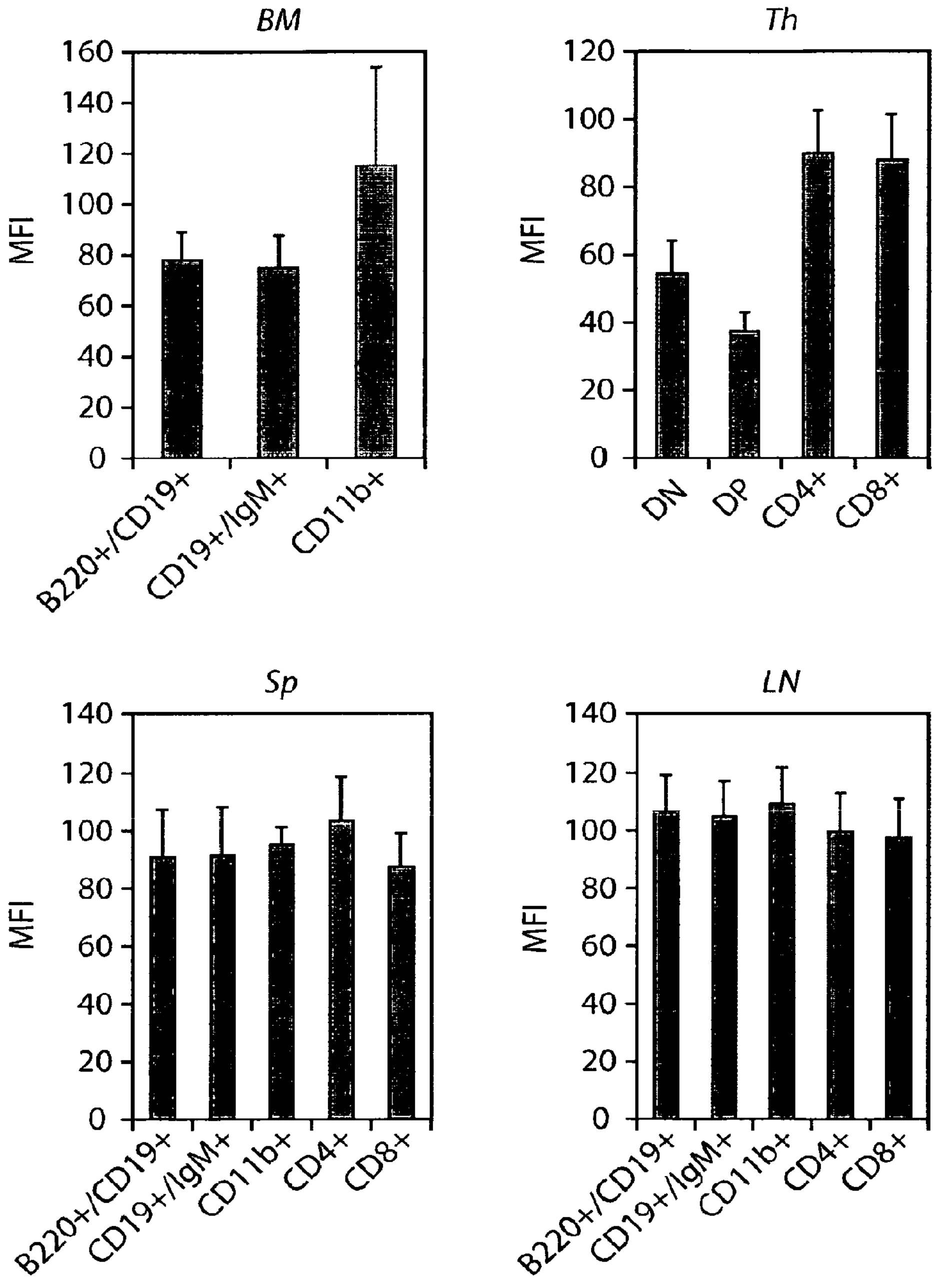
FIG. 1: Coronin 1 expression in T lymphocytes

Coronin 1 is an F-actin interacting protein that is transcribed in all cells of the haematopoietic lineage (G. Ferrari et al., Cell 1999, 97, 435-447). Analysis of the different haematopoietic cell types using FACScan for the expression of coronin 1 reveals that T cells express coronin 1 most abundantly (FIG. 1), with a more moderate expression in B cells and macrophages.

Coronin 1 Deficient Mice

To analyze a role for coronin 1 during T cell stimulation, mice lacking coronin 1 were generated by homologous recombination in embryonic stem cells (FIG. 2*a*). To be able to analyze the in vivo pattern of coronin 1 expression, exon 1 was replaced with the enhanced green fluorescent protein coding region (FIG. 2*a,b*). Coronin 1–/– mice were born at the expected mendelian ratio, were fertile and appeared to be healthy. As expected, thymus and spleen from coronin 1–/– animals lacked any detectable coronin 1 expression, confirming ablation of coronin 1 in lymphocytes (FIG. 2*c*). The morphological appearance as well as the F-actin and tubulin cytoskeleton of the B cells, T cells and macrophages in coronin 1–/– deficient animals was indistinguishable from leukocytes that were isolated from wild type littermates (FIG. 2*d*), suggesting no gross defects in leukocyte cytoskeletal structure and/or morphology.

A contribution of coronin 1 was investigated in lymphocyte development. To that end, bone marrow and thymus from wild type and coronin 1 deficient animals were analyzed for the presence of the different haematopoeitic lineages. Both in the bone marrow as well as in the thymus, lymphocytes appeared to be normal, with no differences in either relative or absolute numbers of lymphocytes present (FIG. 3*a-c*). In the thymus of coronin 1–/– mice, relative subsets of double negative, double positive and single positive T cells were within the normal range of cellularity, although there was a slight but consistent increase in the total number of double positives (FIG. 3*e*). In addition, histological analysis of thymi from wild type and coronin 1–/– mice revealed no differences in the overall organization as well in the proportion of T cell subsets (FIG. 3*d*). Therefore it is concluded that lymphocyte development into CD4 and CD8 single positive T cells occurs normally in the absence of coronin 1.

T Cell Populations in the Periphery

In contrast to normal thymic population and architecture, the analysis of the lymphocyte populations in the periphery reveals gross abnormalities. Analysis of tailblood of coronin 1 deficient animals reveals a drastic reduction in the number of leukocytes, while all other cell types were present in equal numbers (Tables I and II).

TABLE I

Peripheral Blood Composition (ADVIA Analysis)

| | Wild type | Coronin 1 $^{-/-}$ |
|---|---|---|
| Leukocytes (x$10^9$/l) | 15.64 ± 5.77 | 4.77 ± 1.4 |
| Erythrocytes (x$10^{12}$/l) | 10.4 ± 2 | 10.12 ± 1.47 |
| Hemoglobin (g/l) | 161.6 ± 22.53 | 164.05 ± 28.9 |
| Thrombocytes (x$10^9$/l) | 1419.88 ± 265 | 1101.5 ± 265 |
| Reticulocytes (x$10^9$/l) | 413.54 ± 116.1 | 393.4 ± 138.1 |

TABLE II

Peripheral Blood Leukocyte Composition (FACscan Analysis)

| | Wild type | Coronin 1 $^{-/-}$ |
|---|---|---|
| $CD4^+$ (x$10^4$/ml) | 76.6 ± 12.7 | 4.4 ± 2.4 |
| CD8+ (x$10^4$/ml) | 51.2 ± 9.7 | 3.6 ± 2 |
| CD19+ (x$10^4$/ml) | 168.5 ± 48.9 | 48.6 ± 16.9 |
| CD11b+ (x$10^4$/ml) | 64.7 ± 25.4 | 25.8 ± 13 |

Further analysis of the blood reveals that the reduction in leukocyte numbers is largely due to the absence of T lymphocytes. The absence of peripheral T cells in coronin 1–/– deficient animals was confirmed by the analysis of spleen and lymph nodes. The spleen of coronin 1 deficient mice contained ~50% of either CD4 or CD8 positive T cells relative to wild type littermates, while CD19 as well as CD11b positive cells were only slightly depressed (FIG. 4*a,b*). The lymph nodes of coronin 1 deficient mice were however almost completely devoid of T cells when compared to wild type animals (FIG. 4*c,d*). Interestingly, the depletion of T cells was most significant in the inguinal lymph nodes, with a 20-fold difference in single positive T cell numbers, whereas T cells within cervical lymph nodes of coronin –/– mice were reduced (FIG. 4*f*). Histological analysis revealed that T cells were largely depleted from the spleen periarteriolar lymphoid sheets, which were instead filled up with B cells. Although the lymph nodes from coronin 1 deficient mice had only 1/10 of the size of their wild type littermates, the overall architecture was similar to the architecture of wild type littermates (FIG. 4*e*).

Reconstitution of Lymphoid Organs in Wild type and Coronin $1^{-/-}$ mixed Bone Marrow Chimeras To analyze whether the specific depletion of peripheral T cells was reproduced after transplantation of coronin $1^{-/-}$ bone marrow stem cells in irradiated wild type recipient mice, bone marrow cells of coronin $1^{+/+}$ (CD45 allele=$Ly5.1^+$) and coronin $1^{-/-}$ ($Ly5.2^+$) origin separately or in a 50%:50% mixture were transferred into sub-lethally irradiated six weeks old C57BU6 mice (of Ly5.2 origin). After reconstitution, both the thymus as well as the peripheral B cell compartments were reconstituted in an approximate 50:50 ratio (FIG. 5*a,b*) reflecting the capacity of coronin $1^{-/-}$ cells to reconstitute the thymus as well as the B cell compartment. In contrast, the T-lymphocyte populations in the spleen were largely derived from wild type cells (FIG. 5*b*). For lymph nodes, T cells derived from coronin $1^{-/-}$ bone marrow were barely detectible, as judged by the GFP staining, indicating that coronin 1 deficient cells were unable to reconstitute the peripheral T-cell compartments (FIG. 5*b,c*). Similarly, while wild type bone marrow stem cells were able to fully reconstitute the lymphoid system of coronin 1 deficient animals, after transfer of stem cells from coronin 1 deficient mice the resulting animals showed a similar strong defect in the peripheral lymphoid organs as observed in coronin 1 deficient animals (FIG. 5*d-f*). These results therefore further corroborate the finding that in the absence of coronin 1 T-lymphocytes fail to appear or to be maintained in the periphery.

T cell Survival in the Absence of Coronin 1

The absence of thymocytes from the peripheral lymphoid organs could be due to a failure to properly develop in the thymus, a deficiency in T cell homing, or the inability of T cells to survive in the periphery. Since both the cellularity as well as the organization of the thymus in wild type and coronin 1 deficient animals is normal, coronin 1 is unlikely to play a role during T cell development. T cell homing is largely regulated through CD62L (L-selectin), and failure to generate CD62L positive cells in the thymus could be responsible for peripheral T cell depletion. However, as shown in FIG. 6*a*, the percentages of CD62L single positive cells present in the thymus is identical in the presence and absence of coronin 1, suggesting that T cell homing is not compromised in the absence of coronin 1.

To analyze whether the depletion of peripheral T cells occurs through enhanced apoptosis, lymphocytes from thymus, spleen and lymph nodes were analyzed for the expression of annexin V and propidium iodide staining, as markers for apoptosis and necrosis, respectively. Staining of thymocytes revealed identical annexin V and PI positive cell populations, confirming no defects in thymocyte development. In contrast, both within the spleen and lymph nodes the percentage of cells undergoing apopotosis were increased up to 4-fold. In the absence of coronin 1, survival of T cells in the periphery is severely compromised resulting in the induction of apoptosis Coronin 1 in Macrophages Bone marrow derived macrophages isolated from coronin 1 deficient mice showed the absence of coronin 1 by immunoblotting as well as immunostaining on fixed cells, whereas the F-actin and tubulin cytoskeleton was not affected (FIG. 7*a,b*). In addition, motility of macrophages from either wild type or coronin 1 deficient macrophages was found to be similar as analyzed by Transwell assay (FIG. 7*c*). Together these results suggest that coronin 1 does not modulate the macrophage F-actin cytoskeleton in resting or activated conditions.

To directly analyze a role for coronin 1 in phagocytosis, bone marrow macrophages derived from either coronin $1^{-/-}$ mice or wild type littermates were incubated with human serum treated GFP expressing *Lactobacillus casei* or IgG coated fluorescent polystyrene beads for 30 min at 37° C. Both wild type as well as coronin $1^{-/-}$ macrophages were found to have a similar capacity to take up cargo by either complement receptor or Fc receptor-mediated phagocytosis (FIG. 8*a,b*). Similarly, uptake of latex beads, *E. coli* as well as *Salmonella* was found to be identical in macrophages derived from wild type or coronin 1 deficient mice. To analyze a role for coronin 1 in macropinocytosis, wild type or coronin 1 deficient macrophages were incubated with FITC-labeled dextran revealing an identical capacity for macropinocytosis in the presence or absence of coronin 1. Together these data firmly establish that coronin 1 is not essential for phagocytosis or macropinocytosis in macrophages.

In both wild type as well as in coronin 1 deficient macrophages similar numbers of mycobacteria are internalized. However, analysis of the intracellular localization of mycobacteria internalized for 1 hour followed by a 2 hour chase showed that while in wild type macrophages, as expected, mycobacteria were predominantly retained in non-lysosomal phagosomes, in macrophages lacking coronin 1 mycobacteria were largely present in LAMP positive vacuoles (FIG. 9*a,b*). In addition, subcellular fractionation by organelle electrophoresis independently confirmed lysosomal transfer of mycobacteria in coronin 1 deficient macrophages: while in wild type macrophages, mycobacteria were largely retained in non-lysosomal fractions, in coronin 1 deficient macrophages the majority of internalized mycobacteria co-localized with lysosomal organelles (FIG. 9*c*). Finally, whereas wild type mycobacteria survived readily within macrophages, in the absence of coronin 1 mycobacteria were rapidly killed (FIG. 9*d*). Together these results demonstrate that coronin 1 prevented lysosomal delivery and mediated intracellular survival of mycobacteria.

Macrophages from wild type or coronin 1 deficient animals were loaded with the calcium indicator Fluo-3, and cytosolic Ca2+ influx was stimulated using ionomycin. While in macrophages derived from wild type mice the addition of ionomycin was accompanied with a flux of cytosolic $Ca^{2+}$, in the absence of coronin 1 no $Ca^{2+}$ flux was observed upon stimulation, suggesting coronin 1 deficient macrophages, as is the case in T cells, fail to mobilize $Ca^{2+}$ upon stimulation (FIG. 10*a*). Similarly, when Fluo-3 loaded wild type macrophages were allowed to internalize mycobacteria, this internalization was accompanied with mobilization of cytosolic $Ca^{2+}$ in wild type macrophages. In contrast, in macrophages lacking coronin 1, no $Ca^{2+}$ flux was observed following internalization of mycobacteria (FIG. 10*b*).

To analyze whether the coronin 1 mediated $Ca^{2+}$ influx was responsible for the block in lysosomal delivery and survival of mycobacteria, intracellular calcium was chelated before and during the internalization of mycobacteria in macrophages followed by analysis of subcellular delivery and mycobacterial survival. When intracellular calcium was chelated using the cell permeable chelator BAPTA-AM, virtually all mycobacteria were transported to lysosomes and killed, to a similar degree as in coronin 1 deficient macrophages (FIG. 10*c-e*), suggesting that the coronin 1 mediated raise in cytosolic $Ca^{2+}$ was responsible for blocking phagosome-lysosome fusion and intracellular killing of the mycobacteria.

To investigate whether the coronin 1 dependent phagosomal retention and survival of mycobacteria was dependent on gene transcription, mycobacteria were internalized in the presence of the protein synthesis inhibitor cyclohexamide. While cyclohexamide efficiently blocked protein synthesis without compromising macrophage viability, the presence of cycloheximide did not result in alteration of the intracellular routing or survival of mycobacteria (FIG. 10*f*), indicating that the coronin 1 mediated block of phagosome-lysosome fusion did not occur as a result of induction of translation due to the activation of transcription factors.

To analyze whether coronin 1 acts through activation of calcineurin to prevent lysosomal delivery of mycobacteria, the calcineurin inhibitors cyclosporin A and FK506 were analyzed for their ability to induce lysosomal delivery and killing of mycobacteria. Both inhibitors induced a complete relocation of mycobacteria to lysosomes (FIG. 10*g*). Furthermore, mycobacteria were unable to survive within macrophages when calcineurin was blocked by either cyclosporin A or FK506 whereas bacterial proliferation was identical in the presence or absence of calcineurin inhibitors (FIG. 10*h*). Together these results show that coronin 1 dependent calcineurin activation is essential to allow intracellular survival of mycobacteria within macrophages.

Examples

Generation of Coronin 1 Deficient Mice

A targeting vector was constructed to replace the entire exon 2 of coronin 1 by the coding sequence of the enhanced green fluorescent protein (EGFP) followed by a neomycin resistance cassette. The coding region for EGFP was put in frame with the original start codon of the coronin 1 locus leading to expression of EGFP under the control of coronin 1 regulatory elements.

Genomic DNA of mouse embryonic stem cells (129/OIa, TMCF, Biozentrum, Basel, Switzerland) served as a template to amplify by PCR 1.8 kb and 2.7 kb flanking homology regions 5' and 3', respectively, of the start codon for coronin 1. Primers included appropriate restriction sites for further subcloning and have the following sequence: forward primer (5' flanking region): 5'-GCT TAG CGG CCG CGT CAG CAT CTG TTC GGG GG-3' (SEQ ID NO:19); reverse primer (5' flanking homology region): 5'-CGC AGA ATT CCG CCC ATG GGG CTC ATC CTG AAG GAT ACA G-3' (SEQ ID NO:20); forward primer (3' flanking region): 5'-GTG GCA CAC GCC TTT AAT CT-3' (SEQ ID NO:21); reverse primer (3' flanking region): 5'-GCC ATC GCA GAG TGT TGA TA-3' (SEQ ID NO:22). The coding region for EGFP was PCR amplified from pEGFP-N2 (Clontech) using the following primers: forward primer: 5'-CGA ATT CTG CAG TCG ACG GTA CCG-3' (SEQ ID NO:23) and reverse primer: 5'-CGC AGA ATT CGC CTC GAG TTT ACT TGT ACA GCT CGT CC-3' (SEQ ID NO:24). The targeting vector was constructed by first subcloning the 5'-flanking homology region via NotI and EcoRI into pBluescript SK+ (Stratagene). Employing NcoI and EcoRI sites the EGFP cassette was inserted 3' of the 5'-flanking homology region. The 3'-flanking homology region was then added 3' of EGFP by XhoI and EcoRI sites. Via an XhoI site, a SV40polyA signal and the neomycin resistance cassette (pA-lox-TK-Neo-lox, S. Hippenmeyer et al., PLoS Biol 2005, 3, e159) was inserted between EGFP and the 3'-flanking homology region. The ClaI linearized targeting construct was electroporated into mouse embryonic stem cells (strain 129/Sv) and clones were selected with G418. Correctly targeted ES cell clones were identified by Southern blot and then microinjected into C57/BI6xBDF1 blastocysts (RCC, Füllinsdorf, Switzerland). The male chimeras obtained were crossed with C57BU6 females. Transgenic offspring was genotyped by Southern blot to confirm the disruption of the wild-type coronin 1 allele. Mice that were heterozygous for the mutant allele were crossed to generate homozygous coronin 1 deficient mice. Routine PCR screening to specifically detect the mutant allele by the appearance of a 500 bp product was performed with the following primers: forward: 5'-CTG TTG TAG GGG CTG ATG GT-3' (SEQ ID NO:25); reverse: 5'-CTT CAT GTG GTC GGG GTA G-3' (SEQ ID NO:26). The wild type allele is detected by PCR amplifying a 400 bp product with the primers: forward: 5'-CTG TTG TAG GGG CTG ATG GT-3' (SEQ ID NO:27) and reverse: 5'-CAC TGG CCT CAC AGA TCA GA-3' (SEQ ID NO:28).

Biochemical Methods

Cell homogenization, lysis and immunoblotting was performed as described (G. Ferrari et al., Cell 1999, 97, 435-447). Polyclonal anti-coronin 1 serum has been described before (J. Gatfield et al., Mol Biol Cell 2005, 16, 2786-98). Monoclonal anti-GFP was purchased from Roche (monoclonal mouse $IgG_1$, clones 7.1 and 13.1).

For immunoblotting, equal number of cells from both wild type or coronin 1 deficient bone marrow derived macrophages were lysed in Laemmli sample buffer and proteins separated by SDS-PAGE (10%) and transferred on a nitrocellulose membrane. The membrane was probed with anti-coronin 1 antiserum (1:1000 dilution) followed by goat anti-rabbit HRP secondary antibody and developed by enhanced chemoluminescence. For subcellular fractionation, macrophages were homogenized using a ball bearing homogenizer (EMBL, Heidelberg, Germany), and the post-nuclear supernatant was processed for organelle electrophoresis. Bacteria were detected after sedimentation of the different fractions followed by fixation (PFA) and staining with propidium iodide or using acid fast staining (Becton Dickinson).

Immunofluorescence Microscopy

Cells were adhered on poly-L-lysine coated 10 well Teflon-coated glass slides (Polysciences) for 20 minutes on ice. After fixation (10 min, 3% paraformaldehyde in PBS, 37° C.) and permeabilization in 0.1% saponin/2% BSA in PBS, cells were incubated for 30 min with primary antibodies (anti-coronin 1 antiserum, 1:1000; anti-tubulin, $IgG_1$ ascites clone E7, 1:4000). Following washing (3×0.1% saponin/2% BSA in PBS), phalloidin-AlexaFluor568 (Molecular Probes) and secondary antibodies (goat-anti-mouse AlexaFluor568, goat-anti-rabbit AlexaFluor633; Molecular Probes) were applied for 30 min at 1:200 dilutions. Slides were washed 3× with 0.1% saponin/2% BSA in PBS and 3× with PBS and mounted using Fluoroguard antifade mounting medium (Bio-Rad) and analyzed using the confocal laser scanning microscope LSM510 Meta (Zeiss) and the corresponding software.

For macrophage staining, $5\times10^4$ bone marrow derived macrophage cells were seeded on a three well micro slide (Polysciences) and allowed to adhere for 2 h at 37° C. and 5% $CO_2$. 200 μl of *Mycobacterium bovis* BCG suspension, previously washed three times in fresh BMM medium (DMEM supplemented with 30% L292 culture supernatant, 10% FCS, 2 mM glutamine, 0.5 mM 2-mercaptoethanol) and re-suspended to a final OD of 0.2, was replaced gently over the adhered cells and allowed to infect the macrophages for 1 h at 37° C. and 5% $CO_2$. Non-internalized bacteria were removed by three washes with medium, and infected cells were chased for an additional 3 h at the end of which the cells were fixed with methanol and stained for mycobacteria and LAMP1 using rabbit anti *Mycobacterium bovis* polyclonal antibody (Dako), and rat anti LAMP1 monoclonal antibody 1 D4B, respectively. In experiments involving calcineurin inhibitors (cyclosporin A (0.1 μM) and FK506 (0.5 μM)), calcium chelators (BAPTA-AM (1 μM)) or cycloheximide (75 μg/ml) the reagents were added at the time of seeding the macrophages.

Flow Cytometric Analysis and Blood Counts

Cell counts were determined for single cell suspensions of the indicated organs using a Neubauer chamber. Flow cytometry was carried out by staining the cells with the relevant monoclonal antibodies at saturating concentrations in PBS/2% FCS and analyzing them on a FACSCalibur (Becton-Dickinson). The following monoclonal antibodies and secondary reagents were obtained from BD Pharmingen: PE-labelled α-CD19 (clone 1D3), PE-labelled α-B220 (clone RA3-6B2), PE-labelled α-CD3 (clone 145-2C11), PE-labelled α-CD11b (clone M1/70), PECy7-labelled α-CD4 (clone RM4-5), APC-labelled α-CD8a (53-6.7), APC-labelled α-CD62L (clone MEL-14) and PECy7-labelled Streptavidin.

PE-labelled α-CD8a (clone 53-6.7) was obtained from eBioScience. Biotin-labelled antibodies against IgM (clone M41) and CD4 (clone RM4-5) were produced and labelled according to standard techniques. APC-labelled Annexin V (BD Pharmingen) was used according to the manufacturers protocol. Peripheral blood was obtained by tail bleeding and cell counts as well as the hemoglobin concentration were determined on an ADVIA hematology system (Bayer). For flow cytometry, peripheral blood was subjected to erythrocyte lysis prior to staining and analysis on a FACSCalibur.

Immunohistology

Organs were embedded in OCT medium (Sakura Finetek), snap-frozen and 5 μm sections were cut with a cryostat. Sections were air-dried, acetone-fixed for 8 min and stored at −70° C. Sections were then rehydrated and blocked in PBS/2% BSA with 0.1% $NaN_3$ and 220 μg/ml mouse IgG (Jackson ImmunoResearch Laboratories). Antibodies, diluted in PBS/2% BSA, were added directly onto the sections and incubated for 60 min at room temperature in a wet chamber. Antibodies used were: Allophycocyanin (APC)-labelled anti-mouse CD4 (rat IgG2a, clone RM4-5) (Caltag Laboratories), fluorescein isothiocyanate (FITC)-labelled anti-mouse CD8 (rat IgG2a, clone 53-6.7) (BD Biosciences), fluorescein isothiocyanate (FITC)-labelled anti-mouse B220/CD45R (rat IgG2a, clone RA3-6B2) (BD Biosciences), R-Phycoerythrin (PE)-labelled anti-mouse Thy1.2/CD90.2 (mouse IgG2b, clone 5a-8) (Caltag Laboratories) and R-Phycoerythrin (PE)-labelled anti-mouse I-$A^b$ (mouse IgG2a, clone AF6-120.1) (BD Biosciences). Sections were counterstained with dapi (Serva) for 5 min. After washing the sections were mounted in Fluoromount (Southern Biotechnology Associates). Images were taken on a Zeiss Axioskop with ORCA ER camera (Hamamatsu) and images were processed by using OPENLAB software (Improvision, Coventry, U.K.).

Stimulation of T-Lymphocytes

Polystyrene beads (3 or 6 μm diameter; Polysciences) were coated with anti-CD3 (50 μg/ml, clone 145-2C11, BD Pharmingen) antibody in PBS for 1 hr at 37° C. on a shaking thermoblock. Total thymocytes (9×$10^5$) or Ficoll purified splenic lymphocytes (9×$10^5$) were mixed with 1.5×$10^6$ coated beads in IMDM/5% FCS/2 mM glutamine and gently pelleted (250×g, 2 min., 4° C.). Following incubation at 37° C. for 30 min. cells were resuspended in PBS using blunt-ended pipette tips, adhered to poly-L-lysine coated slides and stained for confocal microscopy.

Mixed Bone Marrow Chimeras

Donor bone marrow cells were isolated from either Ly 5.2 positive homozygous coronin 1 knock-out mice or from Ly5.1 positive C57BU6 mice. Bone marrow cells were harvested by flushing isolated femurs and tibias with a syringe and needle using serum-free IMDM. Six weeks old recipient C57BU6 mice (Ly5.2 positive) were irradiated with 950 rad and received then 2×$10^6$ bone marrow cells comprising of a 1:1 mixture of Ly5.$2^+$ coronin 1−/− and Ly5.$1^+$ C57BL/6 cells. As controls irradiated recipients also received 2×$10^6$ of either Ly5.$2^+$ coronin 1−/− or Ly5.$1^+$ C57BL/6 cells alone. Composition and origin of lymphoid cells in chimeric mice was analyzed six weeks later by flow cytometry employing antibody stainings specifically detecting the Ly5.1 or Ly5.2 markers.

Cell Migration

Migration assays were performed in Costar24 well migration chambers with pore size of 8 μm. Cells were laid on the top of the chamber and allowed to migrate towards the bottom half containing chemo attractant (human serum activated zymosan). After 4 h of incubation filters were excised and stained with propidium iodide. Cells were counted using fluorescence microscopy.

Mycobacterial Survival

5×$10^4$ bone marrow derived macrophages in BMM media were seeded per well in a 96 well plate (Costar) and allowed to adhere for 2 h at 37° C. and 5% $CO_2$. 100 μl of *Mycobacterium bovis* BCG washed three times in fresh BMM medium resuspended to a final OD of 0.02 was replaced gently over the adhered cells and allowed to infect the macrophages for 1 h at 37° C. and 5% $CO_2$. Free bacteria were removed by three washes and treatment with amikacin (200 μg/ml) for 1 h. To initiate the chase, 200 μl fresh medium was added per well and chased for the times indicated. At the end of chase, the medium was removed and the macrophages lysed by addition of 100 μl of incorporation media (7H9 medium with 10% DS supplement, 0.15% saponin and 10 μCi/ml of tritiated uracil) to release the intracellular mycobacteria and further incubated for 24 h at 37° C. and 5% $CO_2$. Mycobacteria were lysed by addition of 20 μl of 1N NaOH and incubation at 50° C. for 30 min. Proteins from the lysate were precipitated with 80 μl of 50% trichloro-acetic acid and the supernatant harvested using Packard FilterMate Harvester with Unifilter-96, GF/C filter. The incorporated counts were measured using the TopCount microplate scintillation counter according to the manufacturer's protocol. For experiments involving calcineurin inhibitors or calcium chelators, the reagents were added at the time of seeding of the cells and subsequent steps carried out in the presence of the reagents.

Quantitative Determination of Receptor-Mediated Phagocytosis

To study Fc-receptor mediated phagocytosis 10 μl of a 2% aqueous suspension of yellow-green fluorescent polystyrene beads (Molecular Probes FluoSpheres beads) were washed twice with PBS and then incubated for 1 h at 37° C. on a shaking thermoblock in 1 ml PBS containing 50 μg/ml rabbit IgG (Cappel/ICN). After two additional washing steps in PBS, the IgG-opsonized beads were resupended in 3 ml DMEM/10% FCS/2 mM glutamine. For complement receptor-mediated uptake *Lactobacillus casei* expressing GFP was treated at an $OD_{600}$ of 0.2 with 1:10 diluted fresh or heat-inactivated (56° C., 30 min) human serum in PBS for 30 min at 37° C. on a rotator. Serum treated bacilli were then washed twice in an excess volume of PBS and resuspended in DMEM/10% FCS/2 mM glutamine at an $OD_{600}$ of 2. Bone marrow derived macrophages were seeded to 80% confluency in 24 well cell culture plates (BD Falcon) and shifted to 4° C. followed by the addition of 250 μl per well of the above mentioned suspensions of fluorescent beads or serum treated *Lactobacilli*. To allow phagocytosis, cells were then incubated for 30 min at either 37° C. or 4° C. (cold control) and subsequently washed five times with 1 ml PBS/5% FCS on ice. Cells were harvested by scraping and subjected to flow cytometry (FACSCalibur, Becton Dickinson) to determine uptake of fluorescent cargo in the FL-1 channel. Only living cells as assessed by the forward- and side-scatter profile were considered for the analysis. Rate of uptake was measured as the increase in fluorescence as expressed by the median fluorescence intensity.

Calcium Fluorimetry

Cells were loaded with the calcium specific fluorophore Fluo3 (Molecular Probes) (2 μM) for 1 h at 37° C. and 5% $CO_2$ in the presence of 2.5 mM probenecid. The cells were washed with Ringer's solution without calcium and re-suspended to a final density of 1 million cells per ml. 3 mM Calcium chloride and 2.5 mM probenecid was added and further incubated for 2 h at 37° C. and 5% $CO_2$. After establishment of a base line, cells were stimulated with the solutions indicated after 50 seconds. The fluorescence emission was monitored in channel FL-1 and plotted against time in seconds.

The invention claimed is:

1. A method of induction of immunosuppression following transplantation comprising administering an effective amount of a coronin 1 modulator for immunosuppression to a patient having a transplant, wherein the coronin 1 modulator is selected from the group consisting of:

an anti-coronin 1 polyclonal antibody, monoclonal antibody or an Fab fragment thereof;

a humanized antibody comprising the binding portion of an anti-coronin 1 monoclonal antibody;

a peptide comprising a coronin 1 peptide selected from (SEQ ID NO: 1)
KSRELRVNRGLDTGRRR, (SEQ ID NO: 2)
VSRLEEEMRKLQATVQELQKRLDRLEETVQAK, (SEQ ID NO: 3)
MSRQVVRSSKFRHVFGQPAKADQCYE, (SEQ ID NO: 4)
VCGHTAPVLDIAWCPHNDNVIASGSEDCTVMVWE, (SEQ ID NO: 5)
LEGHTKRVGIVAWHTTAQNVLLSAGCDNVIMVWD, (SEQ ID NO: 6)
PEVHPDTIYSVDWSRDGGLICTSCRDKRVRIIE, (SEQ ID NO: 7)
DRPHEGTRPVRAVFVSEGKILTTGFSRMSERQVALWD,
and (SEQ ID NO: 8)
PLSLQELDTSSGVLLPFFDPDTNIVYLCGKGDSSIRYF;

a phospho-peptide comprising a peptide of the sequence of SEQ ID NO: 1, 2, 3, 4, 5, 6, 7, or 8, wherein one to five serine and/or threonine residues are phosphorylated; and an RNA selected from (SEQ ID NO: 9)
GUUCCGCCACGUGUUUGGA, (SEQ ID NO: 10)
UCCAAACACGUGGCGGAAC, (SEQ ID NO: 11)
GGCCGACCAGUGCUAUGAA, (SEQ ID NO: 12)
UUCAUAGCACUGGUCGGCC, (SEQ ID NO: 13)
GAUGUGCGCGUCUCACAGA, (SEQ ID NO: 14)
UCUGUGAGACGCGCACAUC, -continued (SEQ ID NO: 15)
CCCUAAGUUUGUGGCCCUG, (SEQ ID NO: 16)
CAGGGCCACAAACUUAGGG, (SEQ ID NO: 17)
GUUUGUGGCCCUGAUCUGU,
and (SEQ ID NO: 18)
ACAGAUCAGGGCCACAAAC.

2. The method according to claim 1, wherein the coronin 1 modulator is an anti-coronin 1 polyclonal or monoclonal antibody, or an Fab fragment thereof.

3. The method according to claim 1, wherein the coronin 1 modulator is an anti-coronin 1 Fab fragment.

4. The method according to claim 1, wherein the coronin 1 modulator comprises a peptide of SEQ ID NO: 1, 2, 3, 4, 5, 6, 7 or 8.

5. The method according to claim 1, wherein the coronin 1 modulator is a phospho-peptide comprising a peptide of SEQ ID NO: 1, 2, 3, 4, 5, 6, 7 or 8, wherein one to five serine and/or threonine residues are phosphorylated.

6. The method according to claim 1, wherein the coronin 1 modulator comprises an RNA of the sequence (SEQ ID NO: 9)
GUUCCGCCACGUGUUUGGA, (SEQ ID NO: 10)
UCCAAACACGUGGCGGAAC, (SEQ ID NO: 11)
GGCCGACCAGUGCUAUGAA, (SEQ ID NO: 12)
UUCAUAGCACUGGUCGGCC, (SEQ ID NO: 13)
GAUGUGCGCGUCUCACAGA, (SEQ ID NO: 14)
UCUGUGAGACGCGCACAUC, (SEQ ID NO: 15)
CCCUAAGUUUGUGGCCCUG, (SEQ ID NO: 16)
CAGGGCCACAAACUUAGGG, (SEQ ID NO: 17)
GUUUGUGGCCCUGAUCUGU,
or (SEQ ID NO: 18)
ACAGAUCAGGGCCACAAAC.

* * * * *

SEQUENCE LISTING

```
<160> NUMBER OF SEQ ID NOS: 33

<210> SEQ ID NO 1
<211> LENGTH: 17
<212> TYPE: PRT
<213> ORGANISM: Homo sapiens

<400> SEQUENCE: 1

Lys Ser Arg Glu Leu Arg Val Asn Arg Gly Leu Asp Thr Gly Arg Arg
1               5                   10                  15

Arg


<210> SEQ ID NO 2
<211> LENGTH: 32
<212> TYPE: PRT
<213> ORGANISM: Homo sapiens

<400> SEQUENCE: 2

Val Ser Arg Leu Glu Glu Glu Met Arg Lys Leu Gln Ala Thr Val Gln
1               5                   10                  15

Glu Leu Gln Lys Arg Leu Asp Arg Leu Glu Glu Thr Val Gln Ala Lys
            20                  25                  30


<210> SEQ ID NO 3
<211> LENGTH: 26
<212> TYPE: PRT
<213> ORGANISM: Homo sapiens

<400> SEQUENCE: 3

Met Ser Arg Gln Val Val Arg Ser Ser Lys Phe Arg His Val Phe Gly
1               5                   10                  15

Gln Pro Ala Lys Ala Asp Gln Cys Tyr Glu
            20                  25


<210> SEQ ID NO 4
<211> LENGTH: 34
<212> TYPE: PRT
<213> ORGANISM: Homo sapiens

<400> SEQUENCE: 4

Val Cys Gly His Thr Ala Pro Val Leu Asp Ile Ala Trp Cys Pro His
1               5                   10                  15

Asn Asp Asn Val Ile Ala Ser Gly Ser Glu Asp Cys Thr Val Met Val
            20                  25                  30

Trp Glu


<210> SEQ ID NO 5
<211> LENGTH: 34
<212> TYPE: PRT
<213> ORGANISM: Homo sapiens

<400> SEQUENCE: 5

Leu Glu Gly His Thr Lys Arg Val Gly Ile Val Ala Trp His Thr Thr
1               5                   10                  15

Ala Gln Asn Val Leu Leu Ser Ala Gly Cys Asp Asn Val Ile Met Val
            20                  25                  30
```

-continued

```
Trp Asp


<210> SEQ ID NO 6
<211> LENGTH: 33
<212> TYPE: PRT
<213> ORGANISM: Homo sapiens

<400> SEQUENCE: 6

Pro Glu Val His Pro Asp Thr Ile Tyr Ser Val Asp Trp Ser Arg Asp
1               5                   10                  15

Gly Gly Leu Ile Cys Thr Ser Cys Arg Asp Lys Arg Val Arg Ile Ile
            20                  25                  30

Glu


<210> SEQ ID NO 7
<211> LENGTH: 37
<212> TYPE: PRT
<213> ORGANISM: Homo sapiens

<400> SEQUENCE: 7

Asp Arg Pro His Glu Gly Thr Arg Pro Val Arg Ala Val Phe Val Ser
1               5                   10                  15

Glu Gly Lys Ile Leu Thr Thr Gly Phe Ser Arg Met Ser Glu Arg Gln
            20                  25                  30

Val Ala Leu Trp Asp
        35


<210> SEQ ID NO 8
<211> LENGTH: 38
<212> TYPE: PRT
<213> ORGANISM: Homo sapiens

<400> SEQUENCE: 8

Pro Leu Ser Leu Gln Glu Leu Asp Thr Ser Ser Gly Val Leu Leu Pro
1               5                   10                  15

Phe Phe Asp Pro Asp Thr Asn Ile Val Tyr Leu Cys Gly Lys Gly Asp
            20                  25                  30

Ser Ser Ile Arg Tyr Phe
        35


<210> SEQ ID NO 9
<211> LENGTH: 19
<212> TYPE: RNA
<213> ORGANISM: Homo sapiens

<400> SEQUENCE: 9

guuccgccac guguuugga                                                  19


<210> SEQ ID NO 10
<211> LENGTH: 19
<212> TYPE: RNA
<213> ORGANISM: Homo sapiens

<400> SEQUENCE: 10

uccaaacacg uggcggaac                                                  19


<210> SEQ ID NO 11
<211> LENGTH: 19
<212> TYPE: RNA
<213> ORGANISM: Homo sapiens

<400> SEQUENCE: 11
```

```
ggccgaccag ugcuaugaa                                              19

<210> SEQ ID NO 12
<211> LENGTH: 19
<212> TYPE: RNA
<213> ORGANISM: Homo sapiens

<400> SEQUENCE: 12

uucauagcac uggucggcc                                              19

<210> SEQ ID NO 13
<211> LENGTH: 19
<212> TYPE: RNA
<213> ORGANISM: Homo sapiens

<400> SEQUENCE: 13

gaugugcgcg ucucacaga                                              19

<210> SEQ ID NO 14
<211> LENGTH: 19
<212> TYPE: RNA
<213> ORGANISM: Homo sapiens

<400> SEQUENCE: 14

ucugugagac gcgcacauc                                              19

<210> SEQ ID NO 15
<211> LENGTH: 19
<212> TYPE: RNA
<213> ORGANISM: Homo sapiens

<400> SEQUENCE: 15

cccuaaguuu guggcccug                                              19

<210> SEQ ID NO 16
<211> LENGTH: 19
<212> TYPE: RNA
<213> ORGANISM: Homo sapiens

<400> SEQUENCE: 16

cagggccaca aacuuaggg                                              19

<210> SEQ ID NO 17
<211> LENGTH: 19
<212> TYPE: RNA
<213> ORGANISM: Homo sapiens

<400> SEQUENCE: 17

guuuguggcc cugaucugu                                              19

<210> SEQ ID NO 18
<211> LENGTH: 19
<212> TYPE: RNA
<213> ORGANISM: Homo sapiens

<400> SEQUENCE: 18

acagaucagg gccacaaac                                              19

<210> SEQ ID NO 19
<211> LENGTH: 32
<212> TYPE: DNA
<213> ORGANISM: Artificial sequence
<220> FEATURE:
<223> OTHER INFORMATION: Synthetic Construct- Forward primer for coronin
      1 5' flanking region
```

<400> SEQUENCE: 19
gcttagcggc cgcgtcagca tctgttcggg gg 32

<210> SEQ ID NO 20
<211> LENGTH: 40
<212> TYPE: DNA
<213> ORGANISM: Artificial sequence
<220> FEATURE:
<223> OTHER INFORMATION: Synthetic Construct- Reverse primer for coronin 1 5' flanking region

<400> SEQUENCE: 20
cgcagaattc cgcccatggg gctcatcctg aaggatacag 40

<210> SEQ ID NO 21
<211> LENGTH: 20
<212> TYPE: DNA
<213> ORGANISM: Artificial sequence
<220> FEATURE:
<223> OTHER INFORMATION: Synthetic Construct- Forward primer for Coronin 1 3' flanking region

<400> SEQUENCE: 21
gtggcacacg cctttaatct 20

<210> SEQ ID NO 22
<211> LENGTH: 20
<212> TYPE: DNA
<213> ORGANISM: Artificial sequence
<220> FEATURE:
<223> OTHER INFORMATION: Synthetic Construct- Reverse primer for coronin 1 3' flanking region

<400> SEQUENCE: 22
gccatcgcag agtgttgata 20

<210> SEQ ID NO 23
<211> LENGTH: 24
<212> TYPE: DNA
<213> ORGANISM: Artificial sequence
<220> FEATURE:
<223> OTHER INFORMATION: Synthetic Construct- Forward primer for pEGFP-N2

<400> SEQUENCE: 23
cgaattctgc agtcgacggt accg 24

<210> SEQ ID NO 24
<211> LENGTH: 38
<212> TYPE: DNA
<213> ORGANISM: Artificial sequence
<220> FEATURE:
<223> OTHER INFORMATION: Synthetic Construct- Reverse primer for pEGFP-N2

<400> SEQUENCE: 24
cgcagaattc gcctcgagtt tacttgtaca gctcgtcc 38

<210> SEQ ID NO 25
<211> LENGTH: 20
<212> TYPE: DNA
<213> ORGANISM: Artificial sequence
<220> FEATURE:
<223> OTHER INFORMATION: Synthetic Construct- Forward primer for mutant allele coronin 1 -/-

<400> SEQUENCE: 25

```
ctgttgtagg ggctgatggt                                                20


<210> SEQ ID NO 26
<211> LENGTH: 19
<212> TYPE: DNA
<213> ORGANISM: Artificial sequence
<220> FEATURE:
<223> OTHER INFORMATION: Synthetic Construct- Reverse primer for mutant
      allele coronin 1 -/-

<400> SEQUENCE: 26

cttcatgtgg tcggggtag                                                 19


<210> SEQ ID NO 27
<211> LENGTH: 20
<212> TYPE: DNA
<213> ORGANISM: Artificial sequence
<220> FEATURE:
<223> OTHER INFORMATION: Synthetic Construct- Forward primer for coronin
      1 wild type

<400> SEQUENCE: 27

ctgttgtagg ggctgatggt                                                20


<210> SEQ ID NO 28
<211> LENGTH: 20
<212> TYPE: DNA
<213> ORGANISM: Artificial sequence
<220> FEATURE:
<223> OTHER INFORMATION: Synthetic Construct- Reverse primer for coronin
      1 wild type

<400> SEQUENCE: 28

cactggcctc acagatcaga                                                20


<210> SEQ ID NO 29
<211> LENGTH: 21
<212> TYPE: DNA
<213> ORGANISM: Homo sapiens

<400> SEQUENCE: 29

aagttccgcc acgtgtttgg a                                              21


<210> SEQ ID NO 30
<211> LENGTH: 21
<212> TYPE: DNA
<213> ORGANISM: Homo sapiens

<400> SEQUENCE: 30

aaggccgacc agtgctatga a                                              21


<210> SEQ ID NO 31
<211> LENGTH: 21
<212> TYPE: DNA
<213> ORGANISM: Homo sapiens

<400> SEQUENCE: 31

aagatgtgcg cgtctcacag a                                              21


<210> SEQ ID NO 32
<211> LENGTH: 21
<212> TYPE: DNA
<213> ORGANISM: Homo sapiens

<400> SEQUENCE: 32
```

-continued

```
aaccctaagt ttgtggccct g                                           21


<210> SEQ ID NO 33
<211> LENGTH: 21
<212> TYPE: DNA
<213> ORGANISM: Homo sapiens

<400> SEQUENCE: 33

aagtttgtgg ccctgatctg t                                           21
```